US012797199B2

(12) United States Patent
Yoko et al.

(10) Patent No.: US 12,797,199 B2
(45) Date of Patent: Nov. 17, 2026

(54) CONSTRAINED PROSTHETIC KNEE

(71) Applicant: Zimmer, Inc., Warsaw, IN (US)

(72) Inventors: Tim Yoko, Granger, IN (US); Brian D. Byrd, North Webster, IN (US)

(73) Assignee: Zimmer, Inc., Warsaw, IN (US)

( * ) Notice: Subject to any disclaimer, the term of this patent is extended or adjusted under 35 U.S.C. 154(b) by 330 days.

(21) Appl. No.: 18/526,737

(22) Filed: Dec. 1, 2023

(65) Prior Publication Data

US 2024/0207057 A1 Jun. 27, 2024

Related U.S. Application Data

(60) Provisional application No. 63/434,590, filed on Dec. 22, 2022.

(51) Int. Cl.
*A61F 2/38* (2006.01)
*A61F 2/30* (2006.01)

(52) U.S. Cl.
CPC .. *A61F 2/3845* (2013.01); *A61F 2002/30428* (2013.01); *A61F 2002/30471* (2013.01); *A61F 2002/30528* (2013.01); *A61F 2002/30604* (2013.01); *A61F 2002/30632* (2013.01); *A61F 2002/30639* (2013.01)

(58) Field of Classification Search
CPC ........ A61F 2/38; A61F 2/3845; A61F 2/3836; A61F 2/384; A61F 2/385; A61F 2/3859; A61F 2/3877; A61F 2/389
See application file for complete search history.

(56) References Cited

U.S. PATENT DOCUMENTS

| | | |
|---|---|---|
| 4,262,368 A | 4/1981 | Lacey |
| 4,822,362 A | 4/1989 | Walker et al. |
| 5,139,521 A | 8/1992 | Schelhas |

(Continued)

FOREIGN PATENT DOCUMENTS

| | | |
|---|---|---|
| AU | 2023203769 B2 | 1/2025 |
| AU | 2023285867 | 5/2025 |

(Continued)

OTHER PUBLICATIONS

"Australian Application Serial No. 2023203769, First Examination Report mailed May 16, 2024", 3 pgs.

(Continued)

*Primary Examiner* — Christopher J Beccia
(74) *Attorney, Agent, or Firm* — SCHWEGMAN LUNDBERG & WOESSNER, P.A.

(57) ABSTRACT

A system including a prosthesis assembly for a constrained knee including a tibial baseplate, a mobile bearing, and a fixed bearing. The tibial baseplate can include a distal surface and a proximal surface that can be configured to receive a hinge post. The mobile bearing can be configured to couple with the tibial baseplate and to rotate about at least a first axis approximated by a centerline of the hinge post. The rotation about at least the first axis can be limited by at least the first engagement feature. The fixed bearing can be configured to be coupled to the tibial baseplate. The fixed bearing can be restrained from rotating about the first axis by at least the first engagement feature of the tibial baseplate. The tibial baseplate can be configured to be assembled with either the mobile bearing or the fixed bearing.

19 Claims, 10 Drawing Sheets

(56) References Cited

U.S. PATENT DOCUMENTS

| | | | | |
|---|---|---|---|---|
| 5,282,861 | A | 2/1994 | Kaplan | |
| 5,413,605 | A | 5/1995 | Ashby et al. | |
| 6,162,255 | A | 12/2000 | Oyola | |
| 6,660,039 | B1 | 12/2003 | Evans et al. | |
| 6,911,100 | B1 | 6/2005 | Gibbs et al. | |
| 7,083,652 | B2 | 8/2006 | McCUe et al. | |
| 7,291,174 | B2 | 11/2007 | German et al. | |
| RE44,476 | E | 9/2013 | Meyers et al. | |
| 8,562,616 | B2 | 10/2013 | May et al. | |
| 8,721,733 | B2 | 5/2014 | Bonitati | |
| 8,758,444 | B2 | 6/2014 | Wentorf et al. | |
| 8,936,648 | B2 | 1/2015 | Collard et al. | |
| 9,011,444 | B2 | 4/2015 | Primiano et al. | |
| 9,011,547 | B2 * | 4/2015 | Auger | A61F 2/389 623/20.19 |
| 9,381,090 | B2 | 7/2016 | Wentorf et al. | |
| 9,408,705 | B2 * | 8/2016 | Oosthuizen | A61F 2/38 |
| 9,687,349 | B2 * | 6/2017 | Byrd | A61F 2/08 |
| 9,737,408 | B2 | 8/2017 | Leszko et al. | |
| 10,213,215 | B2 | 2/2019 | Servidio et al. | |
| 10,265,083 | B2 | 4/2019 | Servidio et al. | |
| 10,524,806 | B2 | 1/2020 | Collazo et al. | |
| 10,596,009 | B2 | 3/2020 | Mines et al. | |
| 10,835,382 | B2 | 11/2020 | Habegger et al. | |
| 10,987,225 | B2 | 4/2021 | Yoko et al. | |
| 11,172,940 | B2 | 11/2021 | Servidio et al. | |
| 11,730,603 | B2 | 8/2023 | Zappacosta et al. | |
| 12,369,930 | B2 | 7/2025 | Yoko et al. | |
| 2003/0009228 | A1 | 1/2003 | Meyers et al. | |
| 2003/0055509 | A1 | 3/2003 | McCue et al. | |
| 2003/0171756 | A1 | 9/2003 | Fallin et al. | |
| 2004/0153081 | A1 | 8/2004 | Tulkis et al. | |
| 2004/0267267 | A1 | 12/2004 | Daniels et al. | |
| 2007/0100463 | A1 | 5/2007 | Aram et al. | |
| 2008/0281428 | A1 | 11/2008 | Meyers et al. | |
| 2009/0149964 | A1 | 6/2009 | May et al. | |
| 2009/0270865 | A1 | 10/2009 | Poncet et al. | |
| 2010/0114323 | A1 | 5/2010 | Deruntz et al. | |
| 2010/0174378 | A1 | 7/2010 | Metzger et al. | |
| 2010/0292695 | A1 | 11/2010 | May et al. | |
| 2011/0029092 | A1 | 2/2011 | Deruntz et al. | |
| 2012/0239159 | A1 * | 9/2012 | Metzger | A61F 2/3886 623/20.28 |
| 2012/0323333 | A1 | 12/2012 | Metzger | |
| 2012/0330430 | A1 | 12/2012 | Meyers et al. | |
| 2013/0024001 | A1 | 1/2013 | Wentorf et al. | |
| 2013/0131820 | A1 | 5/2013 | Wentorf et al. | |
| 2013/0150858 | A1 | 6/2013 | Primiano et al. | |
| 2013/0172892 | A1 | 7/2013 | Servidio et al. | |
| 2014/0214172 | A1 | 7/2014 | Hood et al. | |
| 2014/0277528 | A1 | 9/2014 | Mines et al. | |
| 2014/0277540 | A1 | 9/2014 | Leszko et al. | |
| 2015/0202056 | A1 | 7/2015 | Matyas et al. | |
| 2015/0216667 | A1 | 8/2015 | Monaghan | |
| 2017/0000503 | A1 | 1/2017 | Keefer et al. | |
| 2017/0027706 | A1 | 2/2017 | Hagen et al. | |
| 2017/0100254 | A1 | 4/2017 | Lloyd et al. | |
| 2017/0333195 | A1 * | 11/2017 | Wasielewski | A61F 2/3836 |
| 2018/0028324 | A1 | 2/2018 | Clary et al. | |
| 2018/0243100 | A1 | 8/2018 | Boettiger | |
| 2018/0256346 | A1 | 9/2018 | Byrd et al. | |
| 2018/0333267 | A1 | 11/2018 | Landon | |
| 2019/0038417 | A1 | 2/2019 | Yoko et al. | |
| 2021/0015621 | A1 | 1/2021 | Servidio | |
| 2021/0228366 | A1 | 7/2021 | Heggs et al. | |
| 2022/0061998 | A1 | 3/2022 | Zappacosta et al. | |
| 2022/0061999 | A1 | 3/2022 | Zappacosta et al. | |
| 2023/0404603 | A1 | 12/2023 | Yoko et al. | |
| 2024/0207055 | A1 | 6/2024 | Yoko et al. | |
| 2024/0207056 | A1 | 6/2024 | Yoko et al. | |
| 2024/0207058 | A1 | 6/2024 | Yoko et al. | |
| 2024/0207061 | A1 | 6/2024 | Yoko et al. | |
| 2024/0207062 | A1 | 6/2024 | Yoko et al. | |
| 2024/0207063 | A1 | 6/2024 | Yoko et al. | |
| 2025/0152372 | A1 | 5/2025 | Northrop et al. | |
| 2025/0241760 | A1 | 7/2025 | Yoko et al. | |
| 2025/0325282 | A1 | 10/2025 | Yoko et al. | |

FOREIGN PATENT DOCUMENTS

| | | | |
|---|---|---|---|
| AU | 2023285871 | | 7/2025 |
| AU | 2023285872 | | 7/2025 |
| AU | 2023285866 | | 9/2025 |
| AU | 2023285887 | B2 | 12/2025 |
| AU | 2023285874 | B2 | 5/2026 |
| CN | 114869547 | A | 8/2022 |
| CN | 111643230 | | 8/2023 |
| CN | 118236202 | A | 6/2024 |
| CN | 118236203 | A | 6/2024 |
| CN | 118236210 | A | 6/2024 |
| CN | 118236211 | A | 6/2024 |
| CN | 118285966 | A | 7/2024 |
| CN | 119157670 | A | 12/2024 |
| CN | 120478007 | | 8/2025 |
| DE | 102009007724 | A1 | 8/2010 |
| EP | 1325718 | A1 | 7/2003 |
| EP | 2777556 | | 9/2014 |
| EP | 3127510 | A1 | 2/2017 |
| EP | 4349281 | A2 | 4/2024 |
| EP | 4389078 | A1 | 6/2024 |
| EP | 4389079 | A1 | 6/2024 |
| EP | 4389080 | A1 | 6/2024 |
| EP | 4389081 | A1 | 6/2024 |
| EP | 4389082 | A1 | 6/2024 |
| EP | 4389083 | A1 | 6/2024 |
| EP | 4582064 | | 9/2025 |
| FR | 2685631 | A1 | 7/1993 |
| FR | 2696926 | A1 | 4/1994 |
| FR | 2711750 | A1 | 5/1995 |
| FR | 2949668 | A1 | 3/2011 |
| JP | H0850992 | | 2/1996 |
| JP | 2000152950 | A | 6/2000 |
| JP | 2002253586 | A | 9/2002 |
| JP | 2004097817 | A | 4/2004 |
| JP | 2009542373 | A | 12/2009 |
| JP | 2010506622 | A | 3/2010 |
| JP | 2010115487 | A | 5/2010 |
| JP | 2014008411 | A | 1/2014 |
| JP | 2017514589 | A | 6/2017 |
| JP | 2020536670 | A | 12/2020 |
| JP | 2024000537 | A | 1/2024 |
| JP | 2024091504 | A | 7/2024 |
| JP | 2024091514 | A | 7/2024 |
| JP | 2024091533 | A | 7/2024 |
| JP | 2024091539 | A | 7/2024 |
| JP | 2024091541 | A | 7/2024 |
| JP | 2024091560 | A | 7/2024 |
| JP | 7564296 | B2 | 9/2024 |
| JP | 2024169707 | A | 12/2024 |
| JP | 7673169 | | 4/2025 |
| JP | 7689566 | | 5/2025 |
| JP | 2025100988 | | 7/2025 |
| JP | 2025113423 | | 8/2025 |
| JP | 7746362 | | 9/2025 |
| JP | 7777116 | | 11/2025 |
| JP | 7777571 | | 11/2025 |
| JP | 7888521 | | 7/2026 |
| WO | 2013086340 | | 6/2013 |
| WO | WO-2022026256 | A1 | 2/2022 |
| WO | WO-2022169436 | A2 | 8/2022 |

OTHER PUBLICATIONS

"Australian Application Serial No. 2023203769, Response filed Jul. 31, 2024 to First Examination Report mailed May 16, 2024", 15 pgs.

"European Application Serial No. 19819200.7, Summons to Attend Oral Proceedings mailed Jun. 25, 2024", 12 pgs.

"European Application Serial No. 23180479.0, Extended European Search Report mailed May 16, 2024", 14 pgs.

"European Application Serial No. 23180479.0, Partial Supplementary European Search Report mailed Feb. 16, 2024", 13 pgs.

(56) References Cited

OTHER PUBLICATIONS

"European Application Serial No. 23217988.7, Extended European Search Report mailed May 8, 2024", 7 pgs.
"European Application Serial No. 23217999.4, Extended European Search Report mailed May 8, 2024", 6 pgs.
"European Application Serial No. 23218009.1, Extended European Search Report mailed May 7, 2024", 10 pgs.
"European Application Serial No. 23218189.1, Extended European Search Report mailed May 8, 2024", 7 pgs.
"European Application Serial No. 23218191.7, Extended European Search Report mailed May 7, 2024", 7 pgs.
"European Application Serial No. 23218194.1, Extended European Search Report mailed May 10, 2024", 5 pgs.
"European Application Serial No. 23219853.1, Extended European Search Report mailed May 10, 2024", 5 pgs.
"Japanese Application Serial No. 2023-099994, Notification of Reasons for Refusal mailed May 14, 2024", w/ English Translation, 8 pgs.
Rodiger, Wolf, et al., "Flow-Join: Adaptive Skew Handling for Distributed Joins over High-Speed Networks", IEEE 32nd International Conference on Data Engineering (ICDE), Retrieved from the Internet: <https://db.in.tum.de/-roediger/papers/roediger2016flowjoin.pdf>, (2016), 1-12.
"U.S. Appl. No. 18/207,458, Examiner Interview Summary mailed Mar. 31, 2025", 2 pgs.
"U.S. Appl. No. 18/207,458, Notice of Allowance mailed Apr. 9, 2025", 12 pgs.
"Australian Application Serial No. 2023285866, First Examination Report mailed Nov. 19, 2024", 2 pgs.
"Australian Application Serial No. 2023285867, First Examination Report mailed Nov. 19, 2024", 3 pgs.
"Australian Application Serial No. 2023285867, Response filed Jan. 20, 2025 to First Examination Report mailed Nov. 19, 2024", 4 pgs.
"Australian Application Serial No. 2023285871, First Examination Report mailed Nov. 21, 2024", 4 pgs.
"Australian Application Serial No. 2023285871, Response filed Jan. 20, 2025 to First Examination Report mailed Nov. 21, 2024", 12 pgs.
"Australian Application Serial No. 2023285872, First Examination Report mailed Nov. 29, 2024", 4 pgs.
"Australian Application Serial No. 2023285872, Response filed Feb. 11, 2025 to First Examination Report mailed Nov. 29, 2024", 12 pgs.
"Australian Application Serial No. 2023285873, First Examination Report mailed Mar. 18, 2025", 6 pgs.
"Australian Application Serial No. 2023285874, First Examination Report mailed Mar. 18, 2025", 10 pgs.
"Australian Application Serial No. 2023285887, First Examination Report mailed Jan. 10, 2025", 5 pgs.
"Australian Application Serial No. 2023285887, Response filed Mar. 25, 2025 to First Examination Report mailed Jan. 10, 2025", 15 pgs.
"Canadian Application Serial No. 3,203,292, Office Action mailed Oct. 17, 2024", 6 pgs.
"Canadian Application Serial No. 3,203,292, Response filed Feb. 11, 2025 to Office Action mailed Oct. 17, 2024", 17 pgs.
"Canadian Application Serial No. 3,222,784, Examiners Rule 86(2) Report mailed Apr. 9, 2025", 7 pgs.
"Canadian Application Serial No. 3,222,786, Examiners Rule 86(2) Report mailed Apr. 3, 2025", 6 pgs.
"Canadian Application Serial No. 3,222,794, Examiners Rule 86(2) Report mailed Apr. 4, 2025", 8 pgs.
"European Application Serial No. 23180479.0, Response filed Sep. 3, 2024 to Extended European Search Report mailed May 16, 2024", 48 pgs.
"European Application Serial No. 23217988.7, Response filed Jan. 2, 2025 to Extended European Search Report mailed May 8, 2024", 18 pgs.
"European Application Serial No. 23217999.4, Response filed Jan. 2, 2025 to Extended European Search Report mailed May 8, 2024", 47 pgs.
"European Application Serial No. 23218009.1, Response filed Jan. 2, 2025 to Extended European Search Report mailed May 7, 2024", 15 pgs.
"European Application Serial No. 23218189.1, Response filed Dec. 20, 2024 to Extended European Search Report mailed May 8, 2024", 26 pgs.
"European Application Serial No. 23218191.7, Respone filed Nov. 28, 2024 to Extended European Search Report mailed May 7, 2024", 35 pgs.
"European Application Serial No. 23218194.1, Response filed Dec. 9, 2024 to Extended European Search Report mailed May 10, 2024", 27 pgs.
"European Application Serial No. 23219853.1, Response filed Jan. 2, 2025 to Extended European Search Report mailed May 10, 2024", 12 pgs.
"Japanese Application Serial No. 2023-099994, Response filed Aug. 7, 2024 to Notification of Reasons for Refusal mailed May 14, 2024", W/ English Claims, 10 pgs.
"Japanese Application Serial No. 2023-208330, Notification of Reasons for Refusal mailed Nov. 19, 2024", w/ English translation, 8 pgs.
"Japanese Application Serial No. 2023-208330, Response filed Feb. 18, 2025 Notification of Reasons for Refusal mailed Nov. 19, 2024", W/English Claims, 14 pgs.
"Japanese Application Serial No. 2023-209803, Notification of Reasons for Rejection mailed Nov. 5, 2024", W/English Translation, 7 pgs.
"Japanese Application Serial No. 2023-209803, Response filed Feb. 3, 2025 Notification of Reasons for Rejection mailed Nov. 5, 2024", W/ English Claims, 13 pgs.
"Japanese Application Serial No. 2023-211924, Notification of Reasons for Refusal mailed Oct. 22, 2024", w/ English translation, 13 pgs.
"Japanese Application Serial No. 2023-211924, Response filed Jan. 20, 2025 to Notification of Reasons for Refusal mailed Oct. 22, 2024", W/ English Claims, 15 pgs.
"Japanese Application Serial No. 2023-212709, Notification of Reasons for Refusal mailed Nov. 19, 2024", w/ English translation, 8 pgs.
"Japanese Application Serial No. 2023-212709, Response filed Feb. 18, 2025 Notification of Reasons for Refusal mailed Nov. 19, 2024", W/ English Claims, 10 pgs.
"Japanese Application Serial No. 2023-212853, Notification of Reasons for Refusal mailed Nov. 5, 2024", w/ English translation, 9 pgs.
"Japanese Application Serial No. 2023-212853, Response filed Jan. 22, 2025 to Notification of Reasons for Refusal mailed Nov. 5, 2024", w/ English claims, 12 pgs.
"Japanese Application Serial No. 2023-214441, Notification of Reasons for Refusal mailed Nov. 5, 2024", w/ English translation, 8 pgs.
"Japanese Application Serial No. 2023-214441, Response filed Feb. 3, 2025 to Notification of Reasons for Refusal mailed Nov. 5, 2024", W/ English Claims, 9 pgs.
"Australian Application Serial No. 2023285866, Response filed Apr. 22, 2025 to First Examination Report mailed Nov. 19, 2024", 6 pgs.
"Japanese Application Serial No. 2023-212853, Notification of Reasons for Refusal mailed Apr. 15, 2025", w English Translation, 6 pgs.
"Canadian Application Serial No. 3,222,798, Voluntary Amendment filed Apr. 24, 2025", 17 pgs.
"Japanese Application Serial No. 2023-209803, Notification of Reasons for Rejection mailed Apr. 22, 2025", w English Translation, 6 pgs.
"Australian Application Serial No. 2023285887, Subsequent Examination Report mailed Apr. 23, 2025", 3 pgs.
"Canadian Application Serial No. 3,222,792, Examiners Rule 86(2) Report mailed May 6, 2025", 8 pgs.

(56) References Cited

OTHER PUBLICATIONS

"Australian Application Serial No. 2023285873, Response filed May 15, 2025 to First Examination Report mailed Mar. 18, 2025", 10 pgs.
"Japanese Application Serial No. 2023-208330, Notification of Reasons for Refusal mailed May 13, 2025", w English Translation, 4 pgs.
"Japanese Application Serial No. 2023-212709, Notification of Reasons for Refusal mailed May 13, 2025", w English Translation, 5 pgs.
"Australian Application Serial No. 2023285874, Response filed May 22, 2025 to First Examination Report mailed Mar. 18, 2025", 19 pgs.
"Australian Application Serial No. 2023285873, Subsequent Examination Report mailed Jun. 16, 2025", 5 pgs.
"Australian Application Serial No. 2023285874, Subsequent Examination Report mailed Jun. 23, 2025", 4 pgs.
"Australian Application Serial No. 2023285887, Response Filed Jul. 1, 2025 to Subsequent Examination Report mailed Apr. 23, 2025", 12 pgs.
"Canadian Application Serial No. 3,203,292, Examiners Rule 86(2) Report mailed Jul. 3, 2025", 5 pgs.
"Canadian Application Serial No. 3,222,794, Response filed Jul. 9, 2025 to Examiners Rule 86(2) Report mailed Apr. 4, 2025", 26 pgs.
"Canadian Application Serial No. 3,222,784, Response Filed Jul. 22, 2025 to Examiners Rule 86(2) Report mailed Apr. 9, 2025", 44 pgs.
"Japanese Application Serial No. 2023-209803, Response Filed Jul. 9, 2025 to Notification of Reasons for Rejection mailed Apr. 22, 2025", W English Claims, 10 pgs.
"Australian Application Serial No. 2023285887, Subsequent Examination Report mailed Jul. 25, 2025", 3 pgs.
"European Application Serial No. 23218009.1, Communication Pursuant to Article 94(3) EPC mailed Aug. 4, 2025", 6 pgs.
"Canadian Application Serial No. 3,222,786, Response Filed Jul. 29, 2025 to Examiners Rule 86(2) Report mailed Apr. 3, 2025", 18 pgs.
"Japanese Application Serial No. 2023-208330, Response Filed Aug. 7, 2025 to Notification of Reasons for Refusal mailed May 13, 2025", W English Claims, 8 pgs.
"Australian Application Serial No. 2023285873, Response Filed Aug. 19, 2025 to Subsequent Examination Report mailed Jun. 16, 2025", 13 pgs.
"Australian Application Serial No. 2023285874, Response filed Aug. 26, 2025 to Subsequent Examination Report mailed Jun. 23, 2025", 15 pgs.
"Japanese Application Serial No. 2023-212709, Response filed Aug. 5, 2025 to Notification of Reasons for Refusal mailed May 13, 2025", W English Claims, 8 pgs.
"European Application Serial No. 25177112.7, Extended European Search report mailed Aug. 27, 2025", 7 pgs.
"Canadian Application Serial No. 3,222,792, Response Filed Sep. 2, 2025 to Examiners Rule 86(2) Report mailed May 6, 2025", 21 pgs.
"Australian Application Serial No. 2023285873, Subsequent Examiners Report mailed Sep. 16, 2025", 5 pgs.
"Australian Application Serial No. 2023285874, Subsequent Examination Report mailed Sep. 22, 2025", 3 pgs.
"Australian Application Serial No. 2023285887, Response Filed Oct. 20, 2025 to Subsequent Examination Report mailed Jul. 25, 2025", 5 pgs.
"Canadian Application Serial No. 3,222,264, Examiners Rule 86(2) Report mailed Oct. 23, 2025", 5 pgs.
"Canadian Application Serial No. 3,222,786, Examiners Rule 86(2) Report mailed Oct. 30, 2025", 6 pgs.
"Canadian Application Serial No. 3,203,292, Response Filed Oct. 22, 2025 to Examiners Rule 86(2) Report mailed Jul. 3, 2025", 11 pgs.
"Canadian Application Serial No. 3,222,798, Examiners Rule 86(2) Report mailed Oct. 15, 2025", 11 pgs.
"Japanese Application Serial No. 2023-209803, Examiners Decision of Final Refusal mailed Oct. 28, 2025", W English Translation, 3 pgs.
"Canadian Application Serial No. 3,222,106, Examiners Rule 86(2) Report mailed Nov. 24, 2025", 4 pgs.
"European Application Serial No. 23218009.1, Response Filed Nov. 4, 2025 to Communication Pursuant to Article 94(3) EPC mailed Aug. 4, 2025", 48 pgs.
"Australian Application Serial No. 2023285874, Response filed Nov. 25, 2025 to Subsequent Examination Report mailed Sep. 22, 2025", 17 pgs.
"Canadian Application Serial No. 3,222,792, Examiners Rule 86(2) Report mailed Dec. 23, 2025", 7 pgs.
"Australian Application Serial No. 2024264552, First Examination Report mailed Feb. 26, 2026", 5 pgs.
"U.S. Appl. No. 18/526,693, Non Final Office Action mailed Mar. 4, 2026", 9 pgs.
"U.S. Appl. No. 18/526,955, Response filed May 1, 2026 to Restriction Requirement mailed Mar. 3, 2026", 9 pgs.
"U.S. Appl. No. 18/526,955, Restriction Requirement mailed Mar. 3, 2026", 10 pgs.
"U.S. Appl. No. 18/527,961, Non Final Office Action mailed May 22, 2026", 7 pgs.
"U.S. Appl. No. 18/527,961, Notice of Allowance mailed Mar. 30, 2026", 9 pgs.
"U.S. Appl. No. 18/528,003, Response filed May 4, 2026 to Restriction Requirement mailed Mar. 9, 2026", 9 pgs.
"U.S. Appl. No. 18/528,003, Restriction Requirement mailed Mar. 9, 2026", 10 pgs.
"U.S. Appl. No. 18/528,042, Restriction Requirement mailed Apr. 17, 2026", 7 pgs.
"U.S. Appl. No. 18/528,079, Non Final Office Action mailed May 21, 2026", 26 pgs.
"Australian Application Serial No. 2024264552, Response filed May 5, 2026 to First Examination Report mailed Feb. 26, 2026", 23 pgs.
"Canadian Application Serial No. 3,222,106, Response filed Mar. 18, 2026 to Examiners Rule 86(2) Report mailed Nov. 24, 2025", 16 pgs.
"Canadian Application Serial No. 3,222,264, Response filed Feb. 12, 2026 to Examiners Rule 86(2) Report mailed Oct. 23, 2025", W/ English Claims, 61 pgs.
"Canadian Application Serial No. 3,222,786, Response filed Feb. 18, 2026 to Examiners Rule 86(2) Report mailed Oct. 30, 2025", W/ English Claims, 17 pgs.
"Canadian Application Serial No. 3,222,792, Response filed Apr. 20, 2026 to Examiners Rule 86(2) Report mailed Dec. 23, 2025", 16 pgs.
"Canadian Application Serial No. 3,222,798, Response filed Feb. 4, 2026 to Examiners Rule 86(2) Report mailed Oct. 15, 2025", W/ English Claims, 27 pgs.
"European Application Serial No. 23217988.7, Communication Pursuant to Article 94(3) EPC mailed May 19, 2026", 4 pgs.
"European Application Serial No. 23217999.4, Communication Pursuant to Article 94(3) EPC mailed May 21, 2026", 4 pgs.
"European Application Serial No. 23218191.7, Communication Pursuant to Article 94(3) EPC mailed May 12, 2026", 6 pgs.
"European Application Serial No. 23219853.1, Communication Pursuant to Article 94(3) EPC mailed May 7, 2026", 4 pgs.
"European Application Serial No. 25177112.7, Response filed Mar. 23, 2026 to Extended European Search report mailed Aug. 27, 2025", 55 pgs.
"Japanese Application Serial No. 2023-209803, Response filed Feb. 19, 2026 to Examiners Decision of Final Refusal mailed Oct. 28, 2025", W/ English Claims, 15 pgs.
"Japanese Application Serial No. 2024-167426, Notification of Reasons for Refusal mailed Feb. 3, 2026", w/ English Translation, 29 pgs.
"U.S. Appl. No. 18/526/693, Response filed Jun. 1, 2026 to Non Final Office Action mailed Mar. 4, 2026", 8 pgs.
"U.S. Appl. No. 18/528,003, Non Final Office Action mailed Jun. 16, 2026", 13 pgs.

(56) References Cited

OTHER PUBLICATIONS

"U.S. Appl. No. 18/528,042, Response filed Jun. 17, 2026 to Restriction Requirement mailed Apr. 17, 2026", 8 pgs.
"U.S. Appl. No. 18/526,693, Notice of Allowance mailed Jul. 16, 2026", 7 pgs.
"U.S. Appl. No. 19/258,634, Restriction Requirement mailed Aug. 14, 2026", 7 pgs.
"Australian Application Serial No. 2024264552, Subsequent Examiners Report mailed Jun. 3, 2026", 4 pgs.
"Australian Application Serial No. 2025205233, First Examination Report mailed Jun. 10, 2026", 4 pgs.
"Australian Application Serial No. 2025203179, First Examination Report mailed Jun. 15, 2026", 5 pgs.
"Australian Application Serial No. 2025203226, First Examination Report mailed Jun. 4, 2026", 4 pgs.
"Japanese Application Serial No. 2026-081121, Office Action mailed Jun. 16, 2026", W/ Machine English Translation, 6 pgs.
"Japanese Application Serial No. 2026-082079, Office Action mailed Jun. 16, 2026", W/ Machine English Translation, 6 pgs.
"Canadian Application Serial No. 3,222, 106, Examiners Rule 86(2) Report mailed Jun. 5, 2026", 4 pgs.
"Japanese Application Serial No. 2024-167426, Response filed Jun. 10, 2026 to Notification of Reasons for Refusal mailed Feb. 3, 2026", W English Claims, 15 pgs.
"European Application Serial No. 25177112.7, Communication Pursuant to Article 94(3) EPC mailed Jul. 8, 2026", 4 pgs.
"Japanese Application Serial No. 2026-082079, Response filed Jul. 13, 2026 to Office Action mailed Jun. 16, 2026", W English Claims, 91 pgs.
"European Application Serial No. 23219853.1, Response filed Jul. 23, 2026 to Communication Pursuant to Article 94(3) EPC mailed May 7, 2026", 60 pgs.
"Japanese Application Serial No. 2025-071260, Notification of Reasons for Refusal mailed Jul. 14, 2026", w English translation, 7 pgs.

* cited by examiner

CONSTRAINED PROSTHETIC KNEE

CLAIM OF PRIORITY

This application claims the benefit of U.S. Provisional patent application Ser. No. 63/434,590, filed on Dec. 22, 2022, the benefit of priority of which is claimed hereby, and which is incorporated by reference herein in its entirety.

TECHNICAL FIELD

The present disclosure generally relates to orthopedic prostheses. More specifically, the present disclosure relates to orthopedic prostheses used in constrained knee arthroplasties.

BACKGROUND

Orthopedic procedures and prostheses are commonly utilized to repair or replace damaged bone and tissue in the human body. Generally, the knee is formed by the pair of condyles at the distal portion of the femur, the lower surfaces of which bear upon the correspondingly shaped proximal surface plateau of the tibia. The femur and tibia are connected by means of ligaments such as, the posterior cruciate ligament, the lateral collateral ligament, the medial collateral ligament, and the anterior cruciate ligament. These ligaments provide stability to the knee joint.

Prosthetic knee joints can be considered either constrained or unconstrained. Constrained prosthetic knee systems can include femoral and tibial prostheses, which are mechanically linked or constrained to each other to limit relative movement between the femoral and tibial prostheses. Common mechanisms for such mechanical linkage can include a hinge, band, or other linkage structure. An unconstrained prosthetic knee system includes femoral and tibial prostheses, which are not mechanically linked. An unconstrained knee utilizes the existing ligaments and other soft tissue of the patient to provide joint stability. Constrained prosthetic knees have particular applicability to cases where a patient has experienced ligament loss or the existing ligaments do not provide adequate support and stability to the knee.

Overview

This disclosure pertains generally to improved constrained knee prostheses, particularly those utilizing a hinge post. Some constrained knee prostheses with hinge posts utilize a design where the femoral component (and hinge post) are free to move generally proximal/distal relative to the tibial baseplate and the tibial bearing component. The inventors of the present disclosure have recognized the need for a system that provides a prosthesis that can be reconfigured for either a mobile bearing system or a fixed bearing system. The system can include components that can be assembled to form a mobile bearing constrained-knee prosthesis and a fixed constrained-knee prosthesis.

BRIEF DESCRIPTION OF THE DRAWINGS

Various embodiments are illustrated by way of example in the FIGURES of the accompanying drawings. Such embodiments are demonstrative and not intended to be exhaustive or exclusive embodiments of the present subject matter.

DETAILED DESCRIPTION

The present application relates to a system that includes a constrained knee prosthesis. The system can include a set of components, e.g., a tibial tray or baseplate, a shackle, a femoral component, a hinge post, a poly box, an axle bushing, or the like. The set of components can be configured to fit with a tibial bearing component. In examples, the system can include a mobile tibial bearing component or a fixed tibial bearing component, which can be substituted at surgeon discretion. The mobile tibial bearing component can be configured to limit rotation (or movement) about the at least one axis as compared with the mobile tibial bearing component by engaging with one or more engagement features of the tibial tray. The fixed bearing component can prevent or severely limit rotation (or movement) about at least one axis by contacting with one or more engagement features of the tibial tray.

In another example, the system can include the set of components, a mobile tibial bearing component, and a press-fit insert. In such examples, the press-fit insert can be configured to fill the space between the mobile tibial bearing component and one or more engagement features of the tibial tray to further limit or prevent rotation or motion of the tibial bearing component relative to the tibial bearing tray about the one or more axes.

Figure 1:
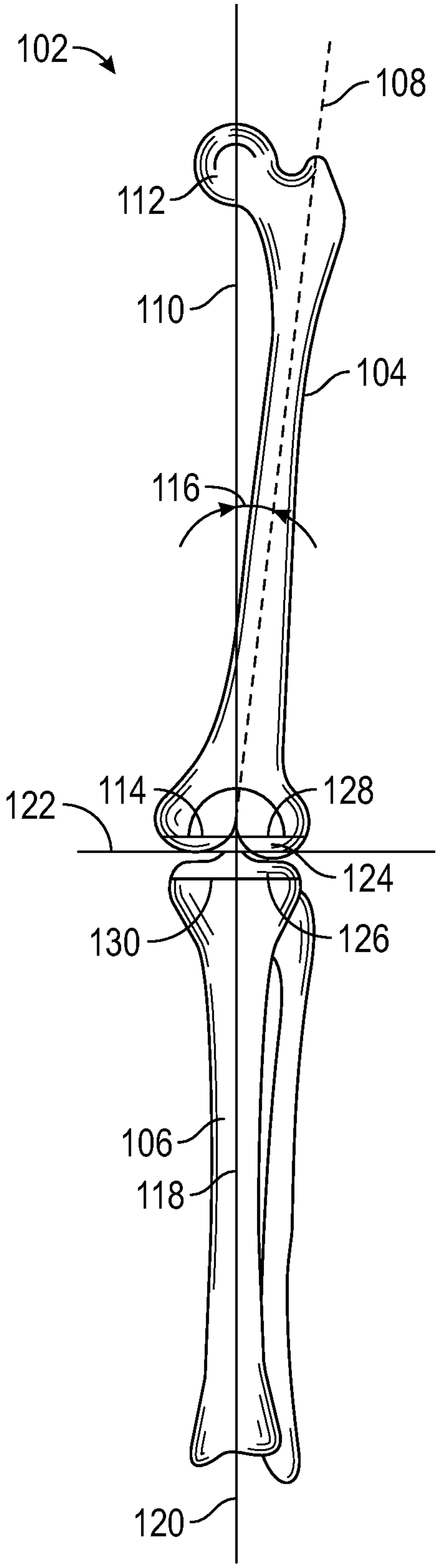
FIGS. 1 and 2 illustrate knee joint structures providing suitable environments in which the constrained prosthesis assemblies in accordance with an example of the present application can be utilized.
Figure 2:
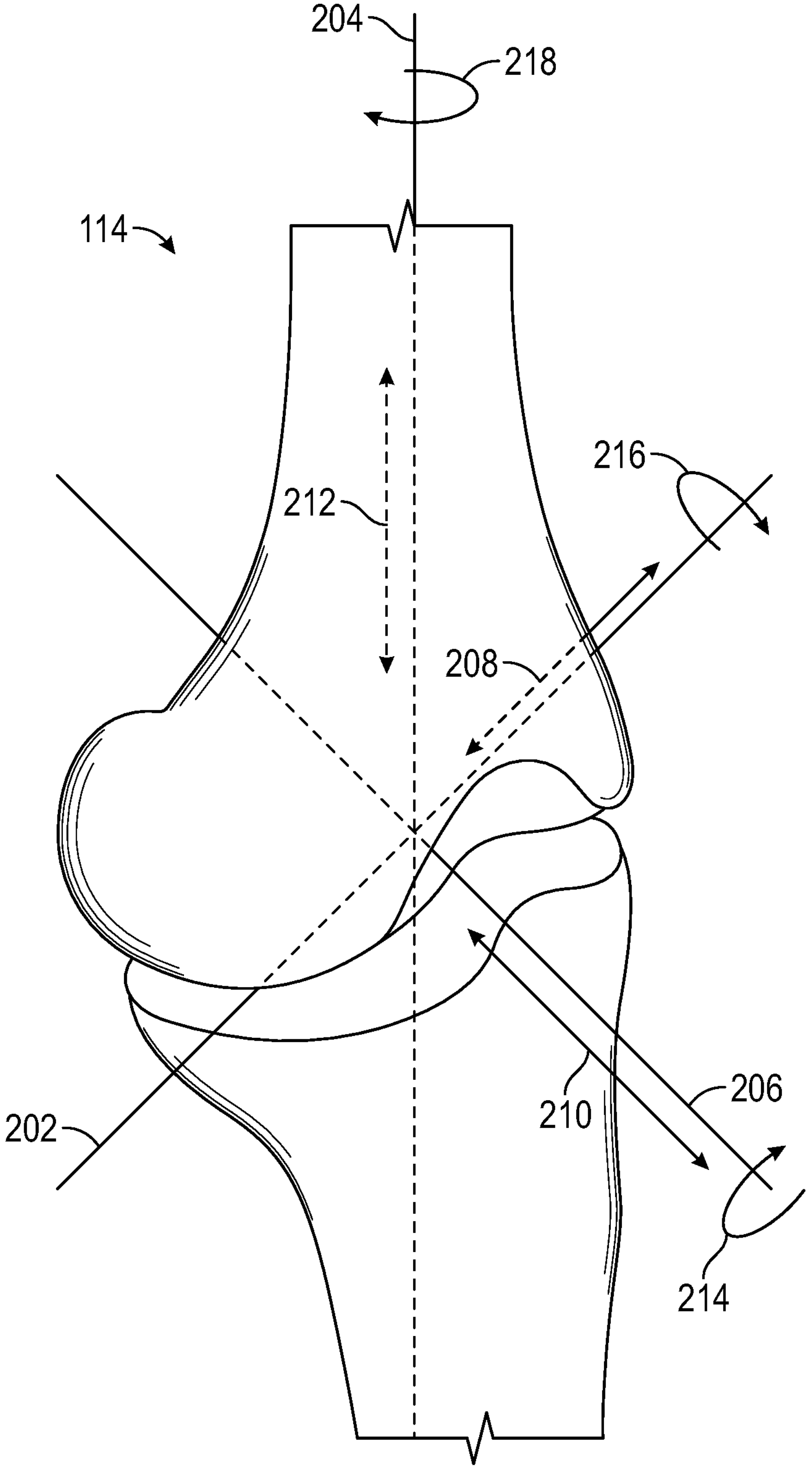

To better understand knee joint replacement procedures, it can be helpful to understand the relationship between bones and bone cuts that can be made to orient various provisional and permanent prosthesis components within a knee joint. FIGS. 1 and 2 illustrate several features of knee joint structures and orientations. In FIG. 1, a frontal view of a lower limb 102, including a femur 104 and a tibia 106, illustrates various lower limb axes. The femur 104 has an anatomic axis 108 that coincides generally with its intramedullary canal. The femur 104 also has a mechanical axis 110, or load axis, running from the center of a femoral head 112 to the center of a knee joint 114. The angle 116 extending between these two axes varies among the patient population but is generally between 5-7 degrees, inclusive. Like the femur 104, the tibia 106 also has an anatomic axis coinciding generally with its intramedullary canal. The mechanical axis 118 of the tibia 106 runs from the center of the knee joint 114 to the center of an ankle region 120 and is generally collinear with its anatomic axis.

A joint line 122, about which the knee joint 114 flexes, is approximately parallel to a line through medial and lateral femoral condyles 124 and to a tibial plateau 126. Although illustrated as perpendicular in FIG. 1, the joint line 122 can extend at a varus or valgus angle relative to the mechanical axes 110 and 118 of the femur 104 and tibia 106, respectively. Normally, during a partial or total knee replacement procedure, portions of a distal end of the femur 104 or a proximal end of the tibia 106 are resected to be parallel or approximately parallel to the joint line 122, and thus perpendicular to the mechanical axes 110 and 118, as indicated at 128 and 130, respectively.

Typical knees can move between an extended state, where a longitudinal axis of the femur 104 and a longitudinal axis of the tibia 106 are essentially parallel, and a flexed state, where the longitudinal axis of the femur 104 and the longitudinal axis of the tibia 106 are angled relative to each other around 140 degrees. In examples, the extended state can be restricted to +/−10 degrees, and the flexed state can be much less than 140 degrees. For example, the flexed state can include limits where the longitudinal axis of the femur 104 and the longitudinal axis of the tibia 106 are angled relative to each other around 90 to 140 degrees.

FIG. 2 illustrates a closer view of the knee joint 114 and its coordinate system, in which a medial/lateral axis 202 corresponds approximately to the joint line 122 (FIG. 1), a proximal/distal axis 204 corresponds approximately to the mechanical axes 110 and 118 (FIG. 1), and an anterior/posterior axis 206 is approximately normal to the other two axes. The arrows can depict positions along each of these axes, representing the medial/lateral 208, anterior/posterior 210, and proximal/distal 212 positioning of inserted prosthesis components. Rotation about each of these axes can also be depicted by arrows. Rotation about the proximal/distal axis 204 can correspond anatomically to external rotation of a femoral component, while rotation about the anterior/posterior axis 206 and medial/lateral axis 202 can correspond to extension plane slope and varus/valgus angle of a component, respectively. Depending on a position of the proximal tibial cut 130 (FIG. 1) made, a varus/valgus angle 214, extension plane angle 216, external rotation 218, or joint extension gap can be affected. Similarly, a position of the distal femoral cut 128 (FIG. 1) can affect the location of the joint line 122, the extension gap, the varus/valgus angle 214, or the extension plane angle 216.

As used herein, the terms “proximal” and “distal” should be given their generally understood anatomical interpretation. The term “proximal” refers to a direction generally toward the torso of a patient, and “distal” refers to the opposite direction of proximal, i.e., away from the torso of a patient. It should be understood that the terms “proximal” and “distal” should be interpreted as though the patient were standing with the knee joint in extension. The intent is to differentiate the terms “proximal” and “distal” from the terms “anterior” and “posterior.” As used herein, the terms “anterior” and “posterior” should be given their generally understood anatomical interpretation. Thus, “posterior” refers to a rear of the patient, e.g., a back of the knee. Similarly, “anterior” refers to a front of the patient, e.g., a front of the knee. Thus, “posterior” refers to the opposite direction of “anterior.” Similarly, the term “lateral” refers to the opposite direction of “medial.” The term “medial/lateral” means medial to lateral or lateral to medial. The term “proximal/distal” means proximal to distal or distal to proximal. The term “anterior/posterior” means anterior to posterior or posterior to anterior.

As used herein, the “periphery” of a tibial baseplate refers to any periphery as viewed in a top plan view, e.g., in a generally transverse anatomical plane. Alternatively, the periphery of a tibial baseplate may be any periphery as viewed in the bottom plan view, e.g., in a generally transverse plane and looking at the distal surface adapted to contact a resected proximal surface of a tibial bone.

The term “micromotion” refers to the small motions that may exist between prosthesis components, such as between the tibial baseplate and capture element, respectively, upon application of force. Such small motions may occur as a result of material deformation in one or both of the interacting components, or may result from slight spaces or clearances therebetween, for example. Micromotion is distinguished from larger movements of components such as the proximal/distal movement of the femoral component relative to the tibial baseplate and the tibial bearing component.

Figure 3:
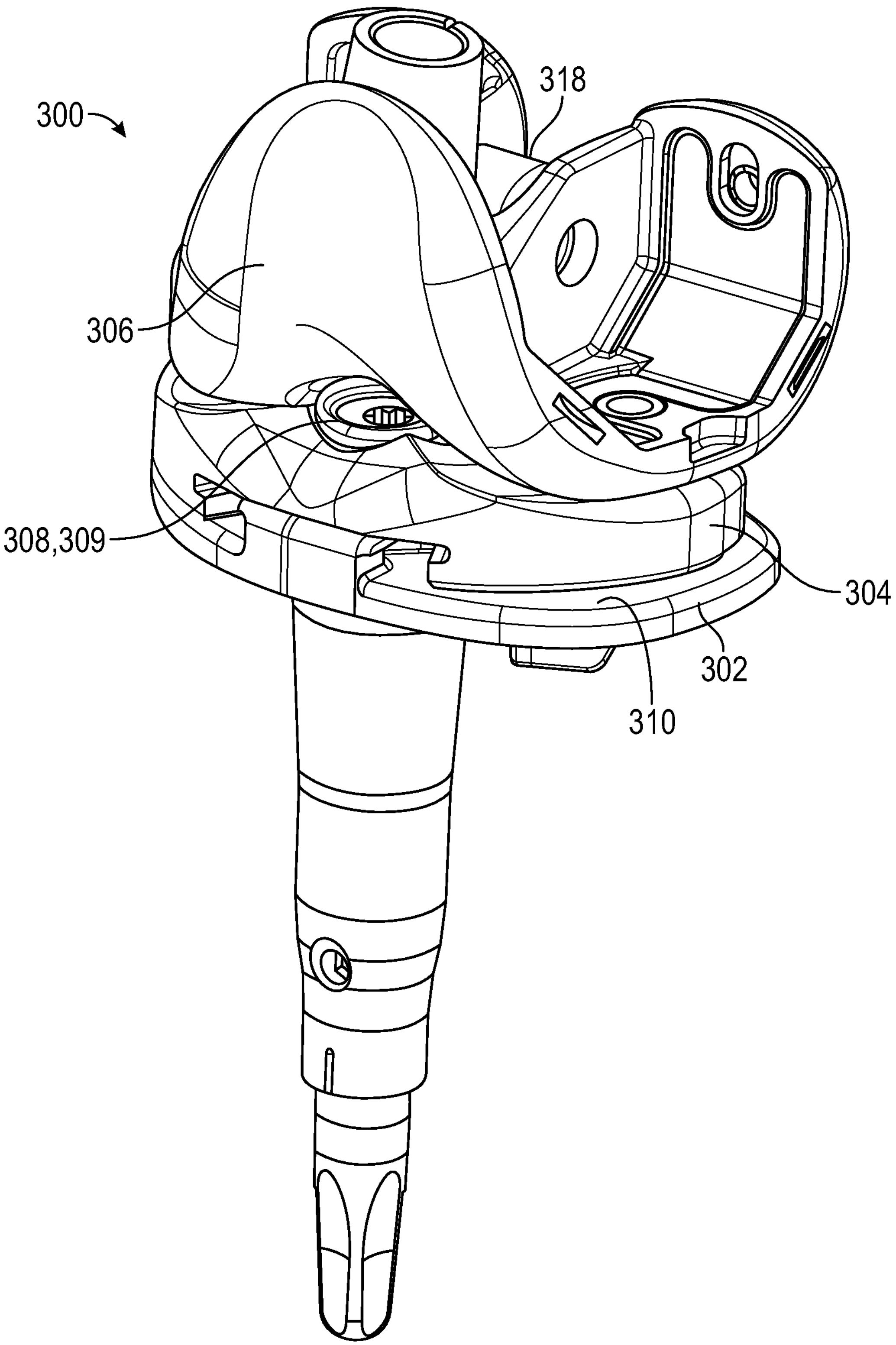
FIG. 3 is a perspective view of a constrained knee prosthesis assembly, according to an example of the present application.

FIG. 3 shows a prosthesis assembly 300 for a constrained knee. The prosthesis assembly 300 can include a tibial baseplate 302, a tibial bearing component 304 (sometime called a meniscal component, poly, articular component or bearing), a femoral component 306 and a hinge post 308.

The tibial bearing component 304 can be coupled to and can be positioned atop a proximal surface 310 of the tibial baseplate 302. The tibial bearing component 304 can be formed of polymer material such as Ultra-High-Molecular-Weight-Polyethylene (“UHMWPE”), or the like. The tibial bearing component 304 can be configured to articulate with the femoral component 306 through knee joint flexion and extension as known in the art. The prosthesis assembly 300 has the femoral component 306 and the tibial baseplate 302 mechanically linked to one another. This is accomplished by the hinge post 308 and other components further illustrated and discussed in FIG. 4. The hinge post 308 is coupled to the femoral component 306 and is received within a recess 309 of the tibial bearing component 304 and a recess 322 (FIG. 4) of the tibial baseplate 302.

Figure 4:
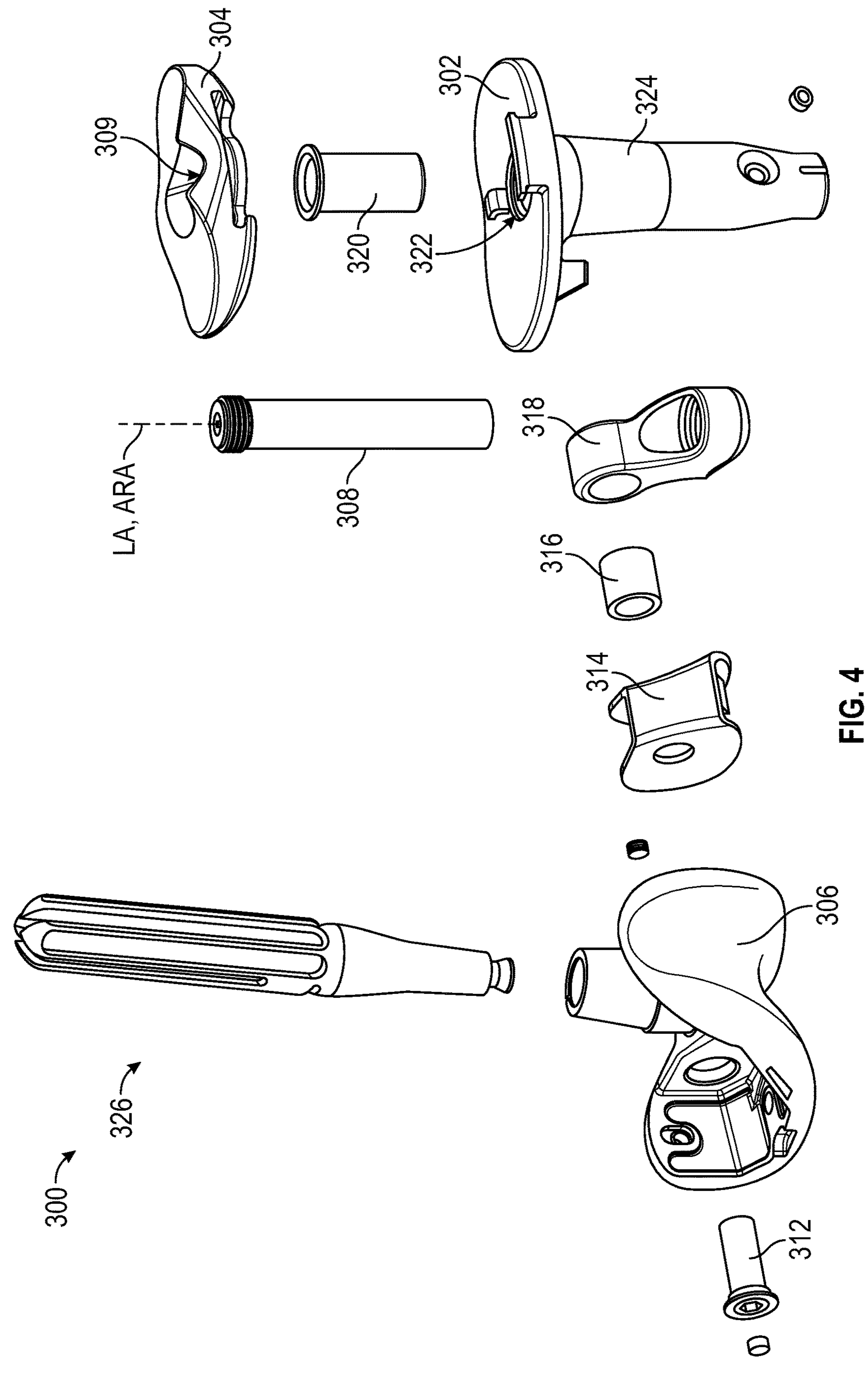
FIG. 4 is an exploded view of the constrained knee prosthesis assembly of FIG. 3, according to an example of the present application.

FIG. 4 shows an exploded view of the prosthesis assembly 300, the tibial baseplate 302, the tibial bearing component 304, the femoral component 306, the hinge post 308 and further illustrates a hinge axle 312, poly box 314, axle bushing 316, shackle 318 and a bushing.

The hinge post 308 is connected to femoral component 306 via the shackle 318, the axle bushing 316, and the hinge axle 312. A distal portion of the shackle 318 is received in the recess 309 in the tibial bearing component 304 and the distal portion is threaded or otherwise connected to the hinge post 308. The hinge post 308 extends distally through the recess 309 of the tibial bearing component 304 and is received in a recess 322 of the tibial baseplate 302. The recess 322 of the tibial baseplate 302 that receives the hinge post 308 can at least partially be formed by a keel 324 of the tibial baseplate 302. The hinge post 308 can be moveable, e.g., rotatable or capable of distraction, relative to the tibial bearing component 304 or the tibial baseplate 302. The hinge post 308 can be rotatably connected to femoral component 306 via the hinge axle 312. Thus, a longitudinal axis LA that defines a centerline of the hinge post 308 can define an axis of rotation/articulation ARA for the knee joint as the femoral component 306 and the tibial baseplate 302 are mechanically linked.

When assembled, the shackle 318 can be placed between opposing walls of poly box 314. When assembled on the hinge axle 312, the axle bushing 316 additionally resides within an aperture on a proximal portion of the shackle 318. The shackle 318 and hinge post 308 can be formed from suitable materials such as a titanium alloy, a cobalt-chromium alloy, or the like, while the axle bushing 316 and the poly box 314 can be formed from different materials such as plastic, e.g., UHMWPE. The axle bushing 316 can act as a bearing between the shackle 318 and the hinge axle 312. The poly box 314 can act as a bearing between the femoral component 306 and the shackle 318.

The prosthesis assembly 300 of FIG. 4 shows a system 326 of components where distraction of the knee is not limited by a capture element or other feature of the prosthesis assembly 300. Thus, the system 326 provides components that, when assembled, are configured for full distraction. Thus, soft tissue of the knee is relied upon to limit distraction between the femoral component 306 and the tibial baseplate 302 and the tibial bearing component 304 as discussed previously. The bushing 320 can be configured to insert into the recess 322 of at least the tibial baseplate 302. The bushing 320 can also insert into or through the recess 309 (FIG. 3) of the tibial bearing component 304 in some examples. The bushing 320 can be configured to receive at least a portion of the hinge post 308. The bushing 320 can act as a bearing between the hinge post 308 and the tibial baseplate 302. The hinge post 308 can be moveable generally proximal/distal relative to the bushing 320.

Figure 5:
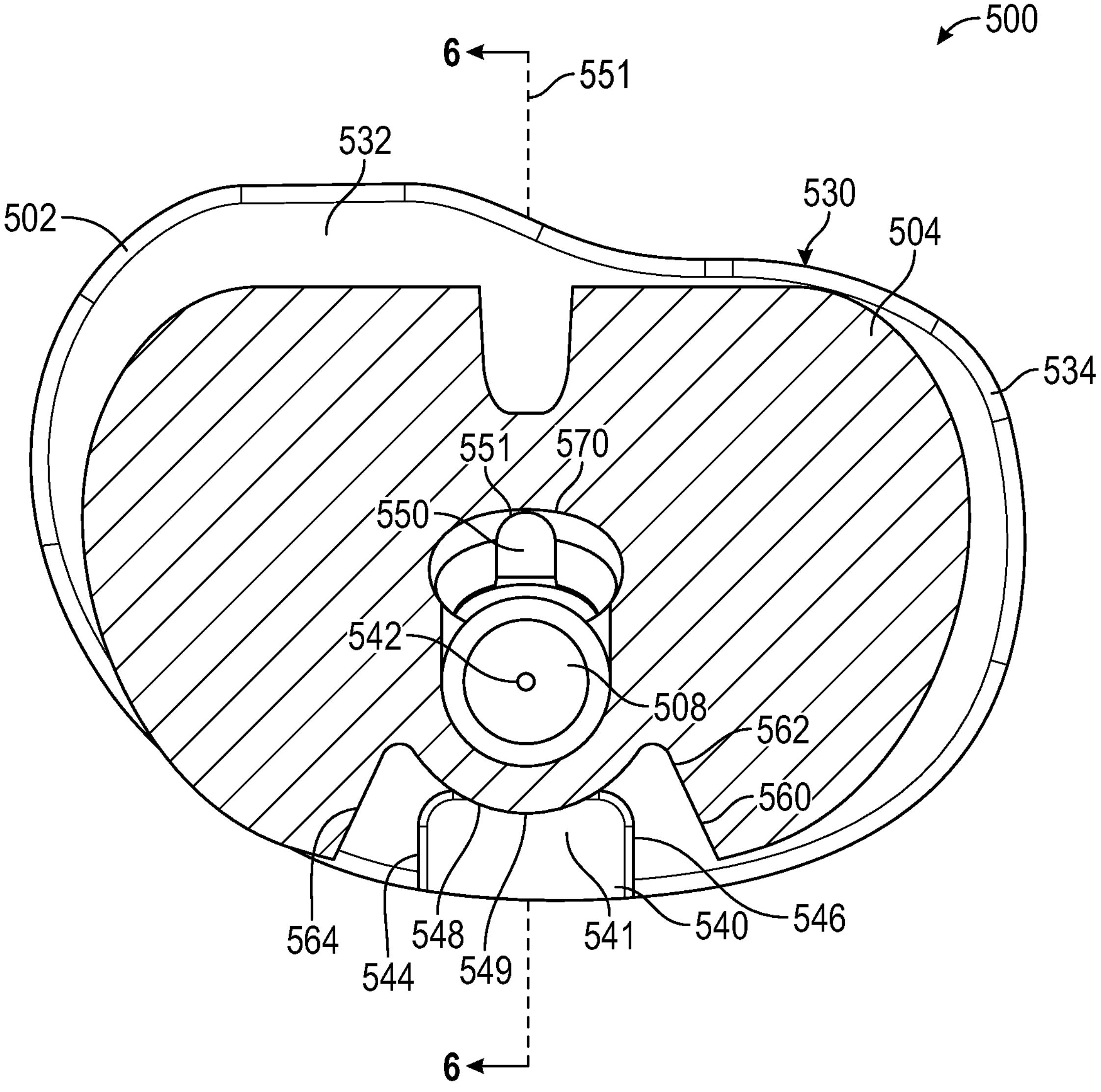
FIG. 5 is a superior view of an example of a constrained knee prosthesis, according to an example of the present application.

FIG. 5 is a superior view of an example of a mobile bearing prosthesis, e.g., a prosthesis assembly 500, according to an example of the present application. The prosthesis assembly 500 can be configured for implant in a constrained knee patient. In examples, the prosthesis assembly 500 can include a tibial baseplate 502, a tibial insert or tibial bearing component (tibial bearing component 504), and a hinge post 508.

The tibial baseplate 502, similar to the tibial baseplate 302 from FIG. 3, can be configured to be inserted into a tibia, e.g., tibia 106 from FIG. 1, of a patient. The tibial baseplate 502 can include a distal surface 530 (shown in FIG. 6) and a proximal surface 532. The proximal surface 532 can be opposite the distal surface 530, and a periphery 534 of the tibial baseplate 502 can extend between the distal surface 530 and the proximal surface 532. The proximal surface 532 can include a recess that is configured to receive the hinge post 508. The proximal surface 532 can also include a first engagement feature 540 and a second engagement feature 550.

The tibial bearing component 504, similar to the tibial bearing component 304 from FIG. 3, can be configured to be coupled to the tibial baseplate 502 and to rotate about at least a first axis 542, e.g., external rotation 218 around distal axis 204 of FIG. 2. In examples, the first axis 542 can extend through a centerline of the hinge post 508. The tibial bearing component 504 can include a third engagement feature 560, and a fourth engagement feature 570.

The first engagement feature 540 can be configured to limit rotation or movement of the tibial bearing component 504 with relation to the tibial baseplate 502 about at least the first axis 542. The first engagement feature 540 can include a protrusion 541. The protrusion 541 can extend from the proximal surface 532 of the tibial baseplate 502. Alternatively, other examples of the present application contemplate that the first engagement feature 540 could be a slot, aperture, or other recess. In the example shown in FIG. 5, the protrusion 541 can extend from an anterior portion of the proximal surface 532 adjacent the periphery 534 and can extend away from the distal surface 530. In another example, the protrusion 541 can extend from a posterior portion, medial portion, lateral portion, or any other portion of the proximal surface 532 that can limit rotation or movement of the tibial bearing component 504 with relation to the tibial baseplate 502 about at least the first axis 542, or the like. The first engagement feature 540 can include a first edge 544, a second edge 546, and a third edge 548.

The first edge 544 can extend posteriorly from the periphery of the tibial baseplate 502. The second edge 546 can also extend posteriorly from the periphery of the tibial baseplate 502. The third edge 548 can extend from the first edge 544 to the second edge 546. The third edge 548 can also include a concave profile 549 such that a thickness of the first engagement feature 540 decreases in a middle portion as compared with the first edge 544 or the second edge 546. In examples, the first edge 544 or the second edge 546 can engage with the tibial bearing component 504 to limit further rotation of the tibial bearing component 504 relative to the tibial baseplate 502 about the first axis 542. The interactions between the tibial bearing component 504 and the first edge 544, the second edge 546, and the third edge 548 of the first engagement feature 540 will be discussed in more detail below with reference to FIGS. 7 and 8.

The third engagement feature 560 can be configured to engage with the first engagement feature 540 of the tibial bearing component 504 to limit rotation of the tibial bearing component 504 relative to the tibial baseplate 502 about at least the first axis 542. The third engagement feature 560 can be an anterior recess that can include a first internal wall 562 and a second internal wall 564. For example, the third engagement feature 560 can be configured to contact the third edge 548 of the first engagement feature 540 upon coupling the tibial bearing component 504 onto the tibial baseplate 502. The contact between the third engagement feature 560 and the third edge 548 can help keep the tibial bearing component 504 on the tibial baseplate 502.

The second internal wall 564 of the third engagement feature 560 can engage with the first edge 544. The first internal wall 562 of the third engagement feature 560 can engage with the second edge 546. Thus, the first internal wall 562 and the second internal wall 564 of the third engagement feature 560 can engage with the second edge 546 and the first edge 544, respectively, to limit rotation in either clockwise or counterclockwise directions of the tibial bearing component 504 relative to the tibial baseplate 502 about the first axis 542. As shown in FIG. 5, the third engagement feature 560 can be formed on an anterior portion of the tibial bearing component 504 adjacent the periphery 534 thereof. In another example, the third engagement feature 560 can be formed in any other portion of the tibial bearing component 504 such that the third engagement feature 560 can limit rotation of the tibial bearing component 504 relative to the tibial baseplate 502 about the first axis 542. The interactions between the third engagement feature 560 and the first engagement feature 540 will be discussed in more detail below with reference to FIGS. 7 and 8.

The second engagement feature 550 can be configured to limit movement of the tibial bearing component 504 with relation to the tibial baseplate 502 along at least second direction 552. The movement of the tibial bearing component 504 along the second direction 552, can be limited by engagement of the second engagement feature 550 and the tibial bearing component 504. As shown in FIG. 5, the second engagement feature 550 can include a protrusion 551 that extends from a central portion of the proximal surface 532 such as adjacent but spaced immediately posterior of the recess that receives the hinge post 508. In another example, the second engagement feature 550 can extend from a posterior, medial, lateral, or any other portion of the proximal surface 532 such that the second engagement feature 550 can limit movement of the tibial bearing component 504 relative to the tibial baseplate 502 along the second direction 552, or the like. The interactions between the tibial bearing component 504 and the second engagement feature 550 will be discussed in more detail below with reference to FIGS. 10 and 8.

The fourth engagement feature 570 can be configured to engage with the second engagement feature 550 of the tibial bearing component 504 to limit movement of the tibial bearing component 504 relative to the tibial baseplate 502 along at least the second direction 552. The fourth engagement feature 570 can be a wall of a recess formed in the tibial bearing component 504. The recess can be centralized and can communicate to receive the hinge post 508 in addition to the second engagement feature 550. The interactions between the fourth engagement feature 570 and the second engagement feature 550 will be discussed in more detail below with reference to FIGS. 10 and 8.

As shown in FIG. 5, the first engagement feature 540 and the second engagement feature 550 of the tibial baseplate 502 can be protrusions, and the third engagement feature 560 and the fourth engagement feature 570 of the tibial bearing component 504 can be walls of recesses. In another example, the first engagement feature 540 and the second engagement feature 550 of the tibial baseplate 502 can be recesses, ridges, grooves, or any other formation formed in the surface of the tibial baseplate 502, or the like, and the third engagement feature 560 and the fourth engagement feature 570 can be protrusions, ridges, extensions, or any other formation that extends from the surface of the tibial bearing component 504, or the like.

Figure 6:
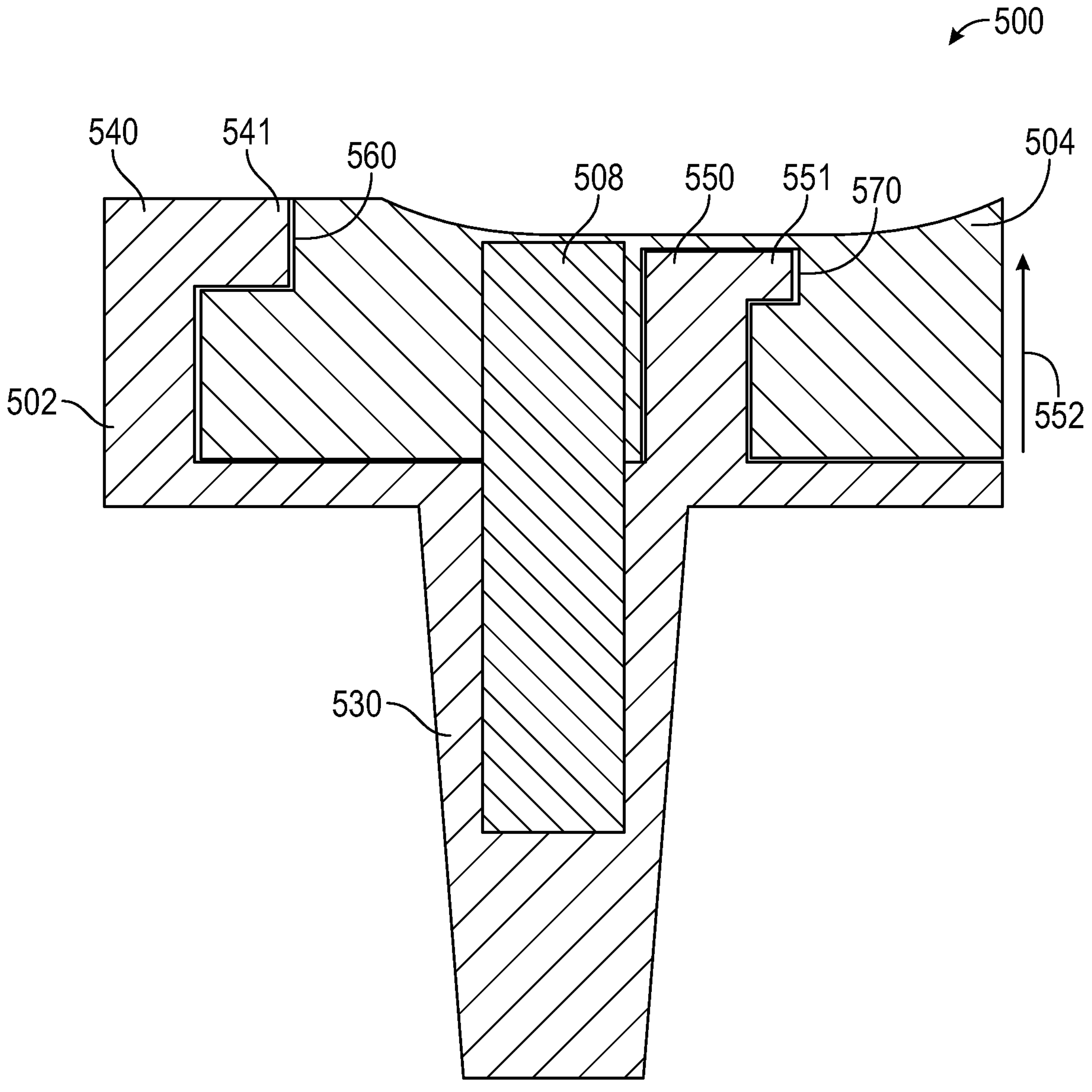
FIG. 6 is a partial cross-sectional view of a constrained knee prosthesis assembly taken along indicator 7-7 of FIG. 5, according to an example of the present application.

FIG. 6 is a partial cross-sectional view of a constrained knee prosthesis assembly, e.g., the prosthesis assembly 500, taken along indicators 7-7 of FIG. 5, according to an example of the present application. As discussed above, and shown in FIG. 6, the tibial bearing component 504 can be configured to be coupled to the tibial baseplate 502. When the tibial bearing component 504 is coupled to the tibial baseplate 502, the third engagement feature 560 and the fourth engagement feature 570 of the tibial bearing component 504 can engage with the first engagement feature 540 and the second engagement feature 550, respectively.

As shown in FIG. 6, the third engagement feature 560 can include a ridge that can be slid under a surface of the protrusion 541 that faces the distal surface 530 of the tibial baseplate 502. The fourth engagement feature 570 can also include a ridge that can be slid under a surface of the protrusion 551 that faces the distal surface 530 of the tibial baseplate 502. As such, during the coupling of the tibial bearing component 504 to the tibial baseplate 502 the ridge of the third engagement feature 560 can be slid under the protrusion 541, and then the ridge of the fourth engagement feature 570 can be slid under the protrusion 551. During the coupling, the first engagement feature 540 and the second engagement feature 550 can be configured such that they flex away from the hinge post 508 and toward the hinge post 508, respectively, to make the coupling of the tibial bearing component 504 to the tibial baseplate 502 easier. Once coupled, the protrusion 541 and the protrusion 551 can engage with the ridges of the third engagement feature 560 and the fourth engagement feature 570, respectively, to prevent the tibial bearing component 504 from moving in the second direction 552 relative to the tibial baseplate 502.

Figure 7:
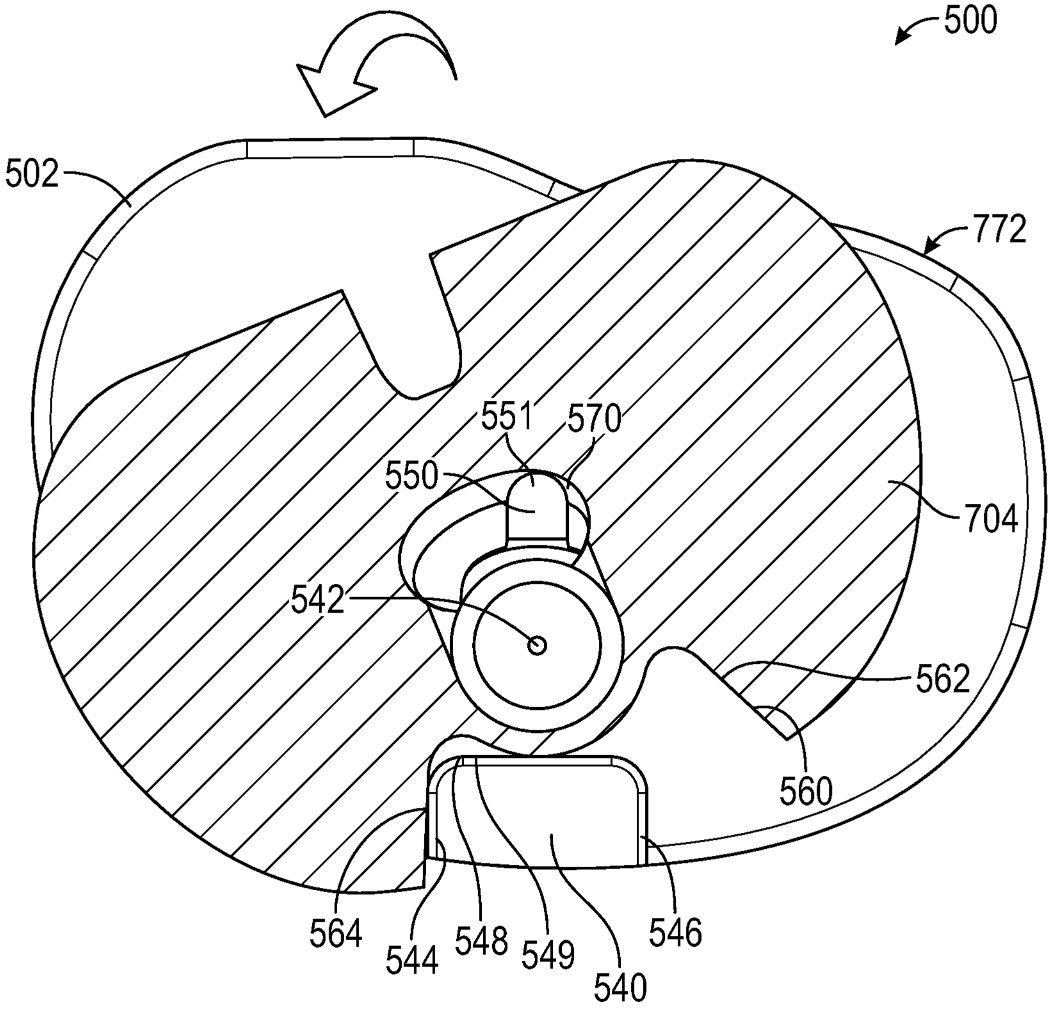
FIG. 7 is a superior view of an example of a constrained knee prosthesis including a mobile bearing rotated to a first set limit, according to an example of the present application.

FIG. 7 is a superior view of an example of a constrained knee prosthesis, e.g., the prosthesis assembly 500, including a mobile bearing 704 rotated to a first set limit, according to an example of the present application. The mobile bearing 704, similar to the tibial bearing component 504 (FIG. 5), can be configured to couple with a tibial baseplate 502. As discussed above, the mobile bearing 704 can rotate about at least a first axis 542 that can be along the centerline of the hinge post 508. As shown in FIG. 7, the mobile bearing 704 can rotate into orientation 772.

In orientation 772, the mobile bearing 704 can rotate counterclockwise in relation to the tibial baseplate 502 about the first axis 542. For example, the mobile bearing 704 can rotate counterclockwise with relation to the tibial baseplate 502 about the first axis 542 until the second internal wall 564 of third engagement feature 560 contacts the first edge 544 of the first engagement feature 540. In such an example, the contact between the second internal wall 564 and the first edge 544 can prevent the mobile bearing 704 from rotating further about the first axis 542 in relation to the tibial baseplate 502. As shown in FIG. 7, the second engagement feature 550 can engage with the fourth engagement feature 570 to prevent the mobile bearing 704 from rotating further about the first axis 542 in relation to the tibial baseplate 502.

Figure 8:
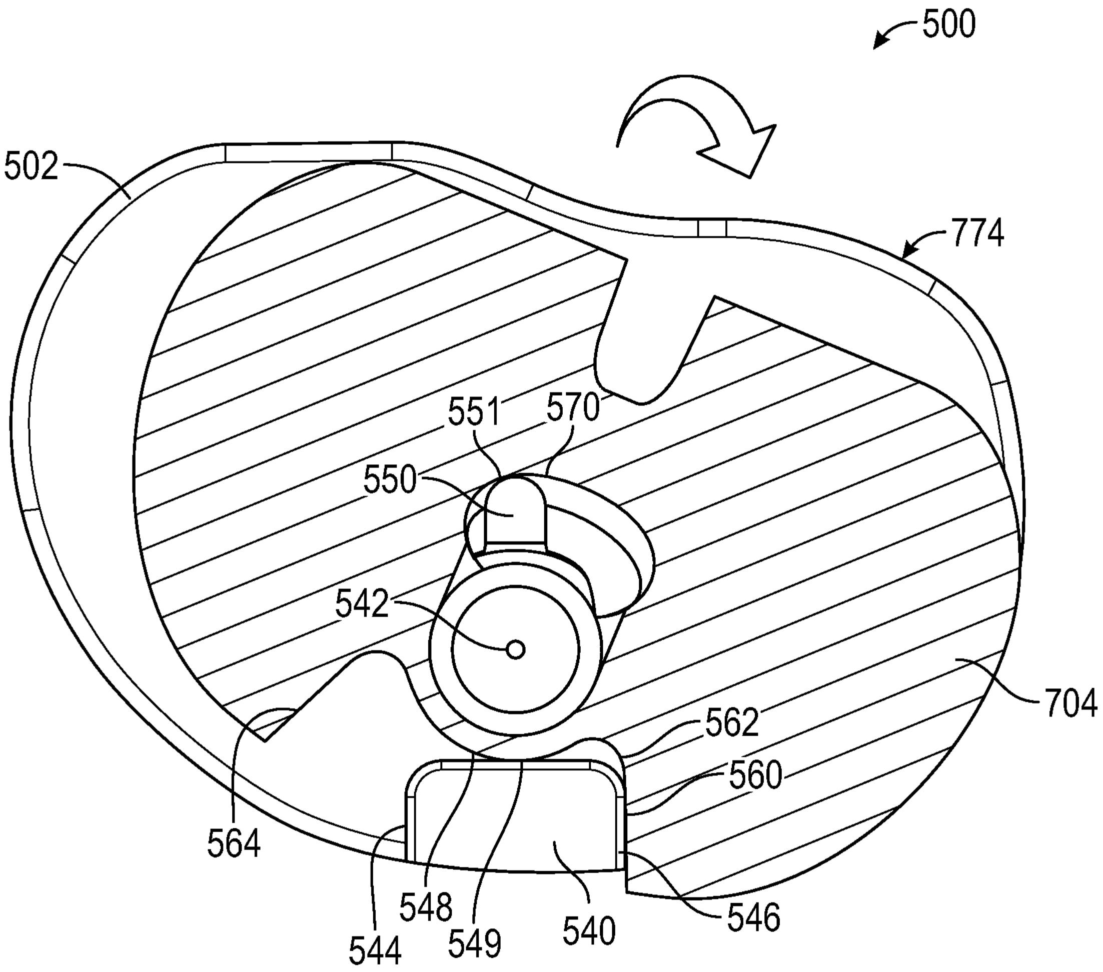
FIG. 8 is a superior view of an example of a constrained knee prosthesis including a mobile bearing rotated to a second set limit, according to an example of the present application.

FIG. 8 is a superior view of an example of a constrained knee prosthesis, e.g., the prosthesis assembly 500, including mobile bearing 704 rotated clockwise to a second set limit, according to an example of the present application. The mobile bearing 704 can rotate clockwise about the first axis 542 with respect to the tibial baseplate 502 to any degree between the orientation 772 and an orientation 774. The prosthesis assembly 500 with the mobile bearing 704 is typically biased more toward a neutral position between the orientation 772 and the orientation 774.

In orientation 774 of FIG. 7, the mobile bearing 704 can rotate with relation to the tibial baseplate 502 about the first axis 542. For example, the mobile bearing 704 can rotate with relation to the tibial baseplate 502 about the first axis 542 until the first internal wall 562 of the third engagement feature 560 contacts the second edge 546 of the first engagement feature 540. In such an example, the contact between the first internal wall 562 and the second edge 546 can prevent the mobile bearing 704 from rotating further about the first axis 542 in relation to the tibial baseplate 502.

Figure 9:
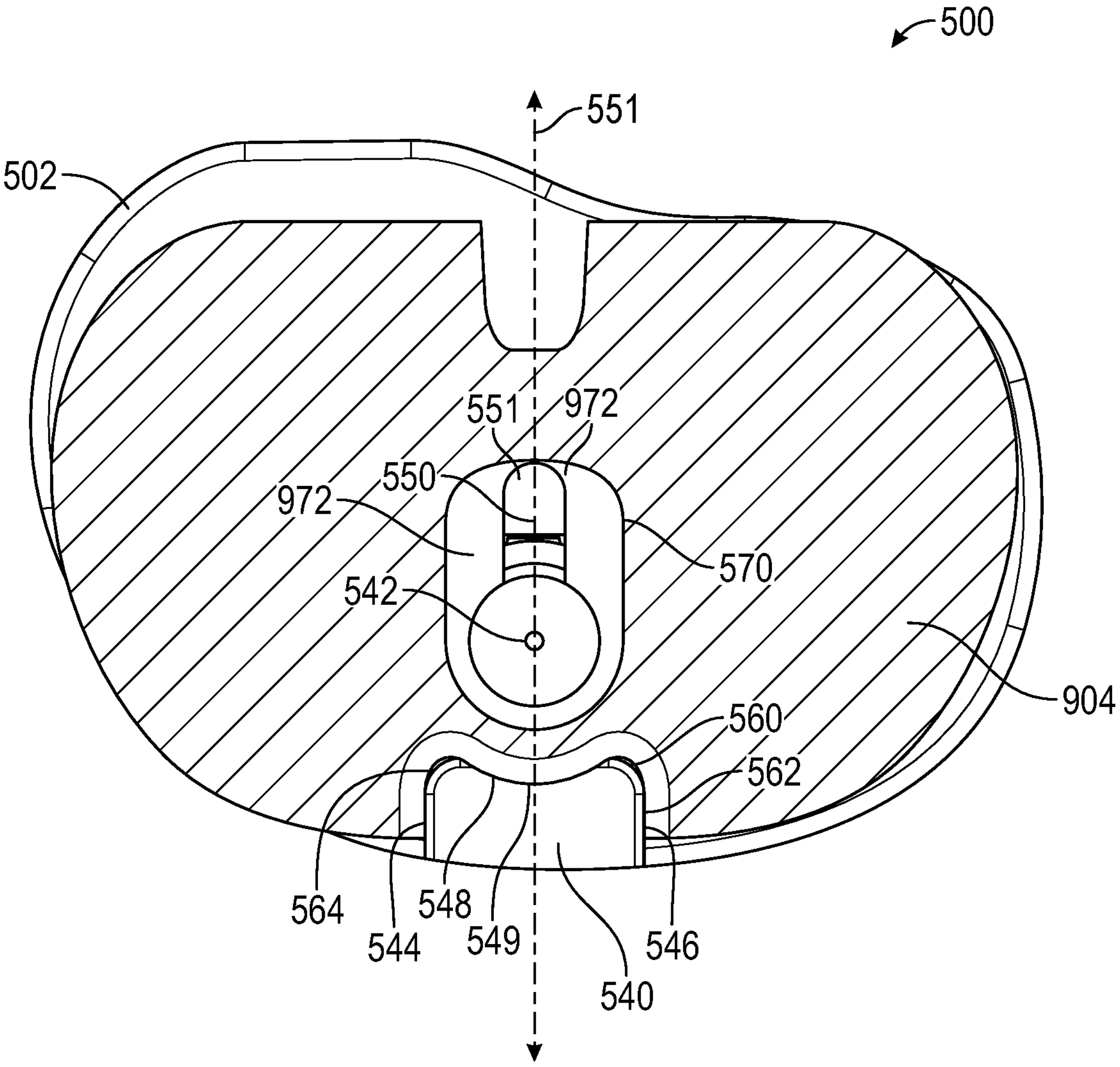
FIG. 9 is a superior view of an example of a constrained knee prosthesis including a fixed bearing, according to an example of the present application.

FIG. 9 is a superior view of an example of a constrained knee prosthesis, e.g., the prosthesis assembly 500, including a fixed bearing 904, according to an example of the present application. The fixed bearing 904, e.g., the tibial bearing component 504 (FIG. 5), can be configured to couple with a tibial baseplate 502. As discussed above, the fixed bearing 904 can prevent rotation or movement of the fixed bearing 904 with relation to the tibial baseplate 502 about the first axis 542 and the second direction 552.

The third engagement feature 560 of the fixed bearing 904 is configured to surround and contact the first engagement feature 540 of the tibial baseplate 502 such as the prevent movement of the fixed bearing 904 relative to the tibial baseplate 502 about the first axis 542. For example, the recess of the third engagement feature 560 that includes first internal wall 562 and second internal wall 564 along the anterior portion of the fixed bearing 904 is smaller than the recess of the third engagement feature 560 on the mobile bearing 704. As such, the first internal wall 562 and the second internal wall 564 of the third engagement feature 560 of the fixed bearing 904 are configured to contact the second edge 546 and the first edge 544, respectively as the fixed bearing 904 is coupled to the tibial baseplate 502. Therefore, the first internal wall 562 and the second internal wall 564 of the fixed bearing 904 prevent rotation of the fixed bearing 904 relative to the tibial baseplate 502 about the first axis 542.

The fourth engagement feature 570 of the fixed bearing 904 is configured to surround and contact the second engagement feature 550 of the tibial baseplate 502 to prevent movement of the fixed bearing 904 relative to the tibial baseplate 502 about the second axis 551. The fourth engagement feature 570 can include flanges, projections, tangs, or ribs (ribs 972). The ribs 972 are configured to surround opposing sides of the second engagement feature 550 and the protrusion 551 to help prevent rotation of the fixed bearing 904 relative to the tibial baseplate 502 about the first axis 542.

Figure 10:
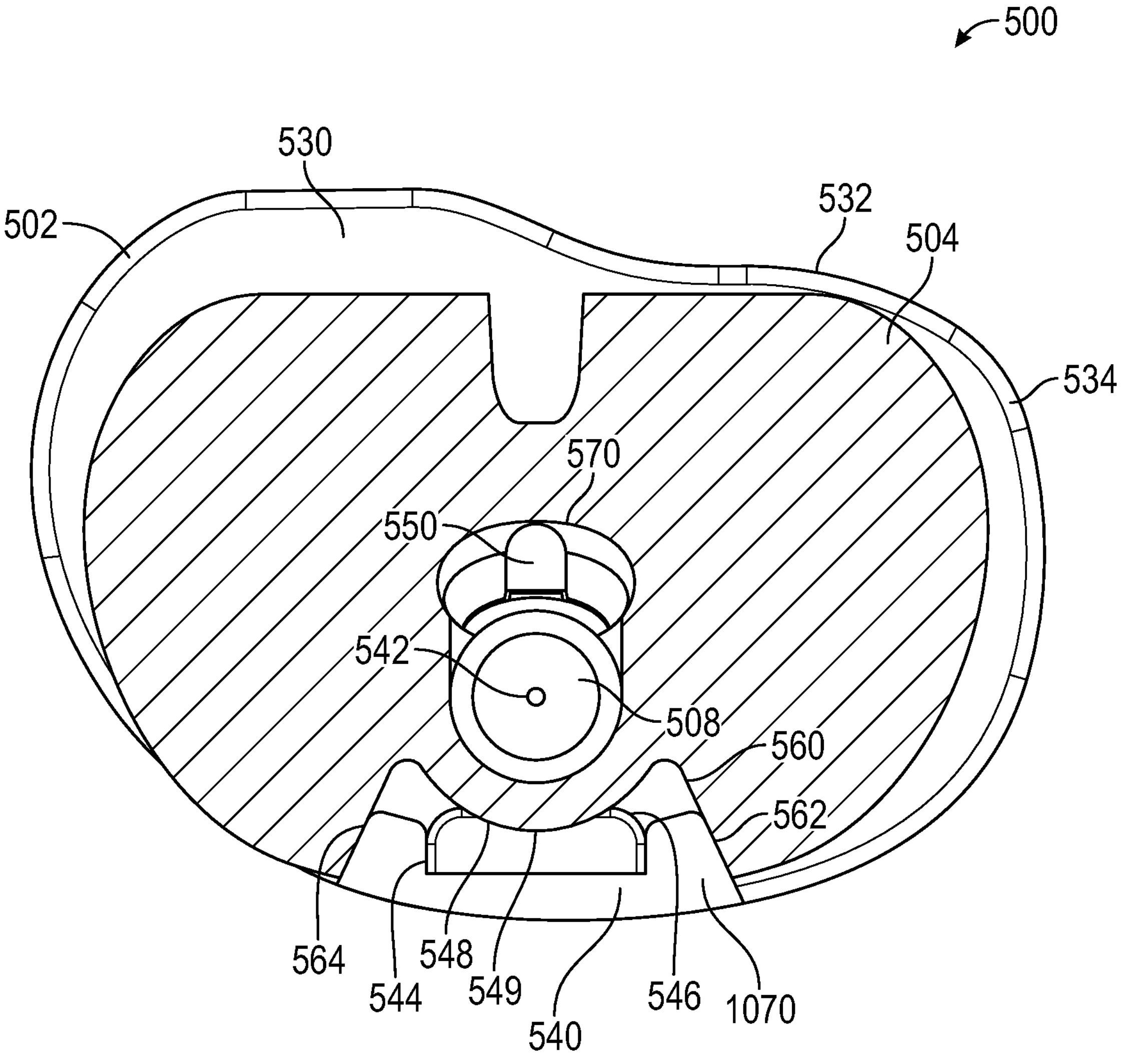
FIG. 10 is a superior view of an example of a constrained knee prosthesis assembly including a mobile bearing with a press-insert, according to an example of the present application.

FIG. 10 is a superior view of an example of a constrained knee prosthesis assembly, e.g., the prosthesis assembly 500, including a mobile bearing, e.g., the mobile bearing 704, with a press fitting 1070, according to an example of the present application.

As discussed above, the prosthesis assembly 500 can be used as a mobile bearing prosthesis by coupling the mobile bearing 704 to the tibial baseplate 502. The prosthesis assembly 500 can be used as a fixed bearing prosthesis by coupling the fixed bearing 904 to the tibial baseplate 502. In another example, the prosthesis assembly 500 can be made a fixed prosthesis by using a press fitting 1070. In examples, the press fitting 1070 can be configured to be inserted into the third engagement feature 560 of the mobile bearing 704. In this example, the press fittings can be configured to fill the space between the first internal wall 562 of the third engagement feature 560 and the second edge 546 of the first engagement feature 540 and configured to fill the gap between the second internal wall 564 of the third engagement feature 560 and the first edge 544 of the first engagement feature 540. Therefore, the press fitting 1070 can effectively turn the mobile bearing 704 into a fixed bearing. As such, the mobile bearing 704 can be coupled onto the tibial baseplate 502 then the press fitting 1070 can be installed onto the mobile bearing 704 such that the press fittings engage with the third engagement feature 560.

As shown in FIG. 10, the first engagement feature 540 can include a slot that extends from a periphery of the mobile bearing 704. The slot can receive the press fitting 1070 such that the press fitting 1070 slides within the slot and surrounds the first engagement feature 540. In the examples of FIG. 10, the press fitting 1070 is configured to fill the entire space between the first edge 544 of the first engagement feature 540 and the second internal wall 564 of the third engagement feature 560 and to fill the entire space between the second edge 546 of the first engagement feature 540 and the first internal wall 562 of the third engagement feature 560. In another example, the press fitting 1070 can be configured to fill any portion of the space between the first edge 544 of the first engagement feature 540 and the second internal wall 564 of the third engagement feature 560 and to fill the space between the second edge 546 of the first engagement feature 540 and the first internal wall 562 of the third engagement feature 560.

Additional Notes & Examples

The following, non-limiting examples, detail certain aspects of the present subject matter to solve the challenges and provide the benefits discussed herein, among others.

Example 1 is a system including a prosthesis assembly for a constrained knee comprising: a set of components including: a femoral component; a shackle component extending between a first end portion and a second end portion; a hinge axle configured to secure the femoral component to the first end portion of the shackle component; a tibial baseplate having a distal surface, a proximal surface opposite the distal surface, a periphery extending between the proximal surface, the tibial baseplate including a first engagement feature; and a hinge post extending between a first end section and a second end section, the first end section configured to be attached to the second end portion of the shackle component, the second end section configured to be at least partially received by a recess in the tibial baseplate; a mobile bearing configured to couple with the tibial baseplate and to rotate about at least a first axis approximated by a centerline of the hinge post, the rotation about at least the first axis is limited by at least the first engagement feature of the tibial baseplate; and a fixed bearing configured to be coupled to the tibial baseplate, the fixed bearing is restrained from rotating about the first axis by at least the first engagement feature of the tibial baseplate; wherein the set of components is configured to be assembled with either the mobile bearing or the fixed bearing.

In Example 2, the subject matter of Example 1 includes, wherein the first engagement feature of the tibial baseplate includes a first protrusion extending from an anterior portion of the proximal surface away from the distal surface.

In Example 3, the subject matter of Example 2 includes, wherein the first protrusion includes: a first edge extending posteriorly from the periphery of the tibial baseplate; a second edge extending posteriorly from the periphery of the tibial baseplate; and a third edge extending from the first edge to the second edge, the third edge includes a concave profile.

In Example 4, the subject matter of Example 3 includes, wherein the tibial baseplate further comprises a second engagement feature.

In Example 5, the subject matter of Example 4 includes, wherein the second engagement feature includes a second protrusion extending from a central portion of the proximal surface and away from the distal surface.

In Example 6, the subject matter of Example 5 includes, wherein the mobile bearing comprises a third engagement feature configured to contact the third edge of the first engagement feature upon coupling of the mobile bearing with the tibial baseplate, the third engagement feature is also configured to engage with the first edge or the second edge of the first engagement feature upon rotation of the mobile bearing about at least the first axis.

In Example 7, the subject matter of Example 6 includes, wherein engagement of the third engagement feature with the first edge and the second edge of the first engagement feature limits the rotation of the mobile bearing.

In Example 8, the subject matter of Examples 6-7 includes, wherein the third engagement feature is formed in an anterior portion of the mobile bearing.

In Example 9, the subject matter of Examples 5-8 includes, wherein the mobile bearing comprises a fourth engagement feature configured to engage with the second engagement feature of the tibial baseplate upon rotation of the mobile bearing about a second axis relative to the tibial baseplate, and wherein engagement of the fourth engagement feature with the second engagement feature limits the rotation of the mobile bearing about the second axis.

In Example 10, the subject matter of Example 9 includes, wherein the fourth engagement feature is formed in the mobile bearing adjacent to a recess configured to receive the hinge post.

In Example 11, the subject matter of Example 10 includes, wherein the fourth engagement feature is posterior to the recess configured to receive the hinge post.

In Example 12, the subject matter of Examples 9-11 includes, wherein the rotation of the mobile bearing about the second axis includes adduction and abduction of the prosthesis assembly.

In Example 13, the subject matter of Examples 4-12 includes, wherein the fixed bearing is configured to engage with the first engagement feature of the tibial baseplate upon coupling of the fixed bearing with the tibial baseplate.

In Example 14, the subject matter of Example 13 includes, wherein the fixed bearing comprises a third engagement feature that contacts the first edge, the second edge, and the third edge of the first engagement feature to prevent rotation of the mobile bearing about at least the first axis.

In Example 15, the subject matter of Examples 13-14 includes, wherein the fixed bearing comprises a fourth engagement feature formed in a central portion of the fixed bearing, the fourth engagement feature contacts the second engagement feature of the tibial baseplate upon coupling of the fixed bearing with the tibial baseplate.

In Example 16, the subject matter of Example 15 includes, wherein the fourth engagement feature includes a pair of ribs that engage the second engagement feature on opposing sides thereof.

Example 17 is a system including a prosthesis assembly for a constrained knee comprising: a tibial baseplate having a distal surface, a proximal surface opposite the distal surface, the proximal surface configured to receive a hinge post, the tibial baseplate including a first engagement feature; a mobile bearing configured to couple with the tibial baseplate and to rotate about at least a first axis approximated by a centerline of the hinge post, the rotation about at least the first axis is limited by at least the first engagement feature; and a fixed bearing configured to be coupled to the tibial baseplate, the fixed bearing is restrained from rotating about the first axis by at least the first engagement feature of the tibial baseplate; wherein the tibial baseplate is configured to be assembled with either the mobile bearing or the fixed bearing.

In Example 18, the subject matter of Example 17 includes, wherein the first engagement feature of the tibial baseplate includes a first protrusion extending from an anterior portion of the proximal surface away from the distal surface.

In Example 19, the subject matter of Example 18 includes, wherein the first protrusion includes: a first edge extending posteriorly from a periphery of the tibial baseplate, the periphery of the tibial baseplate defined by the distal surface and the proximal surface of the tibial baseplate; a second edge extending posteriorly from the periphery of the tibial baseplate; and a third edge extending from the first edge to the second edge, the third edge includes a concave profile.

In Example 20, the subject matter of Example 19 includes, wherein the tibial baseplate further comprises a second engagement feature.

In Example 21, the subject matter of Example 20 includes, wherein the second engagement feature includes a second protrusion extending from a central portion of the proximal surface and away from the distal surface.

In Example 22, the subject matter of Example 21 includes, wherein the mobile bearing comprises a third engagement feature configured to contact the third edge of the first engagement feature upon coupling of the mobile bearing with the tibial baseplate, the third engagement feature is also configured to engage with the first edge or the second edge of the first engagement feature upon rotation of the mobile bearing about at least the first axis.

In Example 23, the subject matter of Example 22 includes, wherein engagement of the third engagement feature with the first edge and the second edge of the first engagement feature limits the rotation of the mobile bearing.

In Example 24, the subject matter of Examples 22-23 includes, wherein the third engagement feature is formed in an anterior portion of the mobile bearing.

In Example 25, the subject matter of Examples 21-24 includes, wherein the mobile bearing comprises a fourth engagement feature configured to engage with the second engagement feature of the tibial baseplate upon rotation of the mobile bearing about a second axis relative to the tibial baseplate, and wherein engagement of the fourth engagement feature with the second engagement feature limits the rotation of the mobile bearing about the second axis.

In Example 26, the subject matter of Example 25 includes, wherein the fourth engagement feature is formed in the mobile bearing adjacent to a recess configured to receive the hinge post.

In Example 27, the subject matter of Example 26 includes, wherein the fourth engagement feature is posterior to the recess configured to receive the hinge post.

In Example 28, the subject matter of Examples 25-27 includes, wherein the rotation of the mobile bearing about the second axis includes adduction and abduction of the prosthesis assembly.

In Example 29, the subject matter of Examples 20-28 includes, wherein the fixed bearing is configured to engage with the first engagement feature of the tibial baseplate upon coupling of the fixed bearing with the tibial baseplate.

In Example 30, the subject matter of Example 29 includes, wherein the fixed bearing comprises a third engagement feature that contacts the first edge, the second edge, and the third edge of the first engagement feature to prevent rotation of the mobile bearing about at least the first axis.

In Example 31, the subject matter of Examples 29-30 includes, wherein the fixed bearing comprises a fourth engagement feature formed in a central portion of the fixed bearing, the fourth engagement feature contacts the second engagement feature of the tibial baseplate upon coupling of the fixed bearing with the tibial baseplate.

In Example 32, the subject matter of Example 31 includes, wherein the fourth engagement feature includes a pair of ribs that engage the second engagement feature on opposing sides thereof.

Example 33 is an apparatus comprising means to implement of any of Examples 1-32.

Example 34 is a system to implement of any of Examples 1-32.

Example 35 is a method to implement of any of Examples 1-32.

Example 36 is a system, method, or apparatus that includes any element of any of examples 1-32.

The above-detailed description includes references to the accompanying drawings, which form a part of the detailed description. The drawings show, by way of illustration, specific embodiments that may be practiced. These embodiments are also referred to herein as "examples." Such examples may include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The term "about," as used herein, means approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 10%. In one aspect, the term "about" means plus or minus 10% of the numerical value of the number with which it is being used. Therefore, about 50% means in the range of 45%-55%. Numerical ranges recited herein by endpoints include all numbers and fractions subsumed within that range, e.g., 1 to 5 includes 1, 1.5, 2, 2.75, 3, 3.90, 4, 4.24, and 5. Similarly, numerical ranges recited herein by endpoints include subranges subsumed within that range, e.g., 1 to 5 includes 1-1.5, 1.5-2, 2-2.75, 2.75-3, 3-3.90, 3.90-4, 4-4.24, 4.24-5, 2-5, 3-5, 1-4, and 2-4. It is also to be understood that all numbers and fractions thereof are presumed to be modified by the term "about."

The above description is intended to be illustrative, and not restrictive. For example, the above-described examples (or one or more aspects thereof) may be used in combination with each other. Other embodiments may be used, such as by one of ordinary skill in the art upon reviewing the above description. The Abstract is to allow the reader to quickly ascertain the nature of the technical disclosure and is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment. The scope of the embodiments should be determined with reference to the appended claims, along with the full scope of equivalents to which such claims are entitled.

The invention claimed is:

1. A system including a prosthesis assembly for a constrained knee comprising:
- a set of components including:
  - a femoral component;
  - a shackle component extending between a first end portion and a second end portion;
  - a hinge axle configured to secure the femoral component to the first end portion of the shackle component;
  - a tibial baseplate having a distal surface, a proximal surface opposite the distal surface, a periphery extending between the proximal surface, the tibial baseplate including a first engagement feature; and
  - a hinge post extending between a first end section and a second end section, the first end section configured to be attached to the second end portion of the shackle component, the second end section configured to be at least partially received by a recess in the tibial baseplate;
- a mobile bearing configured to couple with the tibial baseplate and to rotate about at least a first axis approximated by a centerline of the hinge post, the rotation about at least the first axis is limited by at least the first engagement feature of the tibial baseplate; and
- a fixed bearing configured to be coupled to the tibial baseplate, the fixed bearing is restrained from rotating about the first axis by at least the first engagement feature of the tibial baseplate;
- wherein the set of components is configured to be assembled with either the mobile bearing or the fixed bearing.

2. The system of claim 1, wherein the first engagement feature of the tibial baseplate includes a first protrusion extending from an anterior portion of the proximal surface away from the distal surface.

3. The system of claim 2, wherein the first protrusion includes:
- a first edge extending posteriorly from the periphery of the tibial baseplate;
- a second edge extending posteriorly from the periphery of the tibial baseplate; and
- a third edge extending from the first edge to the second edge, the third edge includes a concave profile.

4. The system of claim 3, wherein the tibial baseplate further comprises a second engagement feature.

5. The system of claim 4, wherein the second engagement feature includes a second protrusion extending from a central portion of the proximal surface and away from the distal surface.

6. The system of claim 5, wherein the mobile bearing comprises a third engagement feature configured to contact the third edge of the first engagement feature upon coupling of the mobile bearing with the tibial baseplate, the third engagement feature is also configured to engage with the first edge or the second edge of the first engagement feature upon rotation of the mobile bearing about at least the first axis.

7. The system of claim 6, wherein engagement of the third engagement feature with the first edge and the second edge of the first engagement feature limits the rotation of the mobile bearing.

8. The system of claim 6, wherein the third engagement feature is formed in an anterior portion of the mobile bearing.

9. The system of claim 5, wherein the mobile bearing comprises a fourth engagement feature configured to engage with the second engagement feature of the tibial baseplate upon rotation of the mobile bearing about a second axis relative to the tibial baseplate, and wherein engagement of the fourth engagement feature with the second engagement feature limits the rotation of the mobile bearing about the second axis.

10. The system of claim 9, wherein the fourth engagement feature is formed in the mobile bearing adjacent to a recess configured to receive the hinge post.

11. The system of claim 10, wherein the fourth engagement feature is posterior to the recess configured to receive the hinge post.

12. The system of claim 9, wherein the rotation of the mobile bearing about the second axis includes adduction and abduction of the prosthesis assembly.

13. The system of claim 4, wherein the fixed bearing is configured to engage with the first engagement feature of the tibial baseplate upon coupling of the fixed bearing with the tibial baseplate.

14. The system of claim 13, wherein the fixed bearing comprises a third engagement feature that contacts the first edge, the second edge, and the third edge of the first engagement feature to prevent rotation of the mobile bearing about at least the first axis.

15. The system of claim 13, wherein the fixed bearing comprises a fourth engagement feature formed in a central portion of the fixed bearing, the fourth engagement feature contacts the second engagement feature of the tibial baseplate upon coupling of the fixed bearing with the tibial baseplate.

16. The system of claim 15, wherein the fourth engagement feature includes a pair of ribs that engage the second engagement feature on opposing sides thereof.

17. A system including a prosthesis assembly for a constrained knee comprising:

a tibial baseplate having a distal surface, a proximal surface opposite the distal surface, the proximal surface configured to receive a hinge post, the tibial baseplate including a first engagement feature;

a mobile bearing configured to couple with the tibial baseplate and to rotate about at least a first axis approximated by a centerline of the hinge post, the rotation about at least the first axis is limited by at least the first engagement feature; and a fixed bearing configured to be coupled to the tibial baseplate, the fixed bearing is restrained from rotating about the first axis by at least the first engagement feature of the tibial baseplate;

wherein the tibial baseplate is configured to be assembled with either the mobile bearing or the fixed bearing; and wherein the first engagement feature of the tibial baseplate includes a first protrusion extending from an anterior portion of the proximal surface away from the distal surface, and wherein the first protrusion includes:

a first edge extending posteriorly from a periphery of the tibial baseplate, the periphery of the tibial baseplate defined by the distal surface and the proximal surface of the tibial baseplate;

a second edge extending posteriorly from the periphery of the tibial baseplate; and a third edge extending from the first edge to the second edge, the third edge includes a concave profile.

18. The system of claim 17, wherein the tibial baseplate further comprises a second engagement feature including a second protrusion extending from a central portion of the proximal surface and away from the distal surface, wherein the mobile bearing comprises a third engagement feature configured to contact the third edge of the first engagement feature upon coupling of the mobile bearing with the tibial baseplate, the third engagement feature is also configured to engage with the first edge or the second edge of the first engagement feature upon rotation of the mobile bearing about at least the first axis, and wherein engagement of the third engagement feature with the first edge and the second edge of the first engagement feature limits the rotation of the mobile bearing.

19. The system of claim 18, wherein the mobile bearing comprises a fourth engagement feature configured to engage with the second engagement feature of the tibial baseplate upon rotation of the mobile bearing about a second axis relative to the tibial baseplate, wherein engagement of the fourth engagement feature with the second engagement feature limits the rotation of the mobile bearing about the second axis, wherein the fourth engagement feature is formed in the mobile bearing adjacent to a recess configured to receive the hinge post, wherein the fourth engagement feature is posterior to the recess configured to receive the hinge post, and wherein the rotation of the mobile bearing about the second axis includes adduction and abduction of the prosthesis assembly.

* * * * *